US010519506B2

(12) United States Patent
Goel et al.

(10) Patent No.: US 10,519,506 B2
(45) Date of Patent: Dec. 31, 2019

(54) IDENTIFICATION OF METASTASIS-SPECIFIC MIRNA AND HYPOMETHYLATION SIGNATURES IN HUMAN COLORECTAL CANCER

(71) Applicant: Baylor Research Institute, Dallas, TX (US)

(72) Inventors: Ajay Goel, Dallas, TX (US); C. Richard Boland, Dallas, TX (US); Keun Hur, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 144 days.

(21) Appl. No.: 14/367,827

(22) PCT Filed: Dec. 21, 2012

(86) PCT No.: PCT/US2012/071455
§ 371 (c)(1),
(2) Date: Jun. 20, 2014

(87) PCT Pub. No.: WO2013/096888
PCT Pub. Date: Jun. 27, 2013

(65) Prior Publication Data
US 2015/0072341 A1 Mar. 12, 2015

Related U.S. Application Data

(63) Continuation of application No. 13/725,402, filed on Dec. 21, 2012, now abandoned.

(60) Provisional application No. 61/579,361, filed on Dec. 22, 2011.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2525/207* (2013.01); *C12Q 2600/154* (2013.01); *C12Q 2600/178* (2013.01)

(58) Field of Classification Search
None
See application file for complete search history.

(56) References Cited

U.S. PATENT DOCUMENTS

| 7,871,769 | B2 | 1/2011 | Baker et al. ............... 435/6.14 |
| 2006/0019270 | A1 | 1/2006 | Yang et al. ............... 435/6 |
| 2010/0298410 | A1* | 11/2010 | Obad ............... C12N 15/111 514/44 A |
| 2011/0039272 | A1 | 2/2011 | Cowens et al. ............... 435/6 |
| 2011/0183859 | A1 | 7/2011 | Harris et al. ............... 506/7 |

FOREIGN PATENT DOCUMENTS

| EP | 2196542 | 6/2010 |
| WO | WO 2008/055158 | 5/2008 |
| WO | WO 2009/111643 | 9/2009 |
| WO | WO 2011/128900 | 10/2011 |

OTHER PUBLICATIONS

Lu et al, Nature 435: 834 (2005).*
Barbarotto et al, Int. J. Cancer 122: 969 (2008).*
Bartley et al, Clin. Cancer Res. 17 (23), 7783 (First published Sep. 23, 2011).*
Extended European Search Report Issued in European Patent Application No. 12859326.6, dated Nov. 19, 2015.
Ahn, Joong Bae, et al., "DNA Methylation Predicts Recurrence from Resected Stage 3 Proximal Colon Cancer," Cancer, May 1, 2011, I17(9):1847-1854.
Burke et al., Postgrad Med J, 1996, vol. 72, pp. 464-469.
Choi et al., Modern Pathology, 2007, vol. 20, pp. 802-810.
Cruickshanks et al., Genomics, 2009, vol. 94, pp. 397-406.
Figueiredo et al., Cancer Epidemiol Biomarkers Prev, 2009, vol. 18, pp. 1041-1049.
Huang, et al., "MicroRNA expression profile in non-cancerous colonic tissue associated with lymph node metastasis of colon cancer." Journal of Digestive Diseases (Impact Factor: 1.85). Sep. 2009; 10(3):188-94.
Hur, K. et al. "Abstract 95: Increased hypomethylation of Line-1 and Alu in human colorectal cancer metastasis" Proceedings of the 102$^{nd}$ Annual Meeting of the American Association for Cancer Research; Apr. 2-6, 2011, Cancer Research Apr. 15, 2011, vol. 71, Issue 8, Supplement 1.
Hur, K. et al "Identification of a Novel Metastasis-Specific miRNA Signature in Human Colorectal Cancer" Digestive Disease Week, May 19-22, 2012, Gastroenterology, May 2012, vol. 142, No. 5, Supplement 1, pp. S525-S526; Meeting Abstract.
Kwon, Hyeong-Ju, et al., "DNA Methylation Changes in Ex-Adenoma Carcinoma of the Large Intestine," Circhows Arch, (2010), 457:433-441.

(Continued)

*Primary Examiner* — James Martinell
(74) *Attorney, Agent, or Firm* — Norton Rose Fulbright US LLP

(57) ABSTRACT

The present invention includes methods and biomarkers for diagnosing or detecting colorectal cancer metastasis in a human subject by comparing the Alu repeat methylation level in the biological sample to an Alu repeat methylation control level from a normal non-cancerous sample from the human subject, wherein a decrease in the Alu repeat methylation level is indicative of colorectal cancer and colorectal cancer metastasis. The invention also includes methods and biomarkers for diagnosing or detecting colorectal cancer (CRC) metastasis in a human subject by determining a level of expression of let-7i, miR-10b, miR-320a, and miR-221 in the sample from the one or more biological samples; and comparing the level of expression of let-7i, miR-10b, miR-320a, and miR-221 in the sample with the level of expression of let-7i, miR-10b, miR-320a, and miR-221 from normal colorectal tissue, wherein high expression of at least on of let-7i or miR-320a is indicative of a good prognosis for the CRC, while the low expression of at least one of miR-10b or miR-221 is indicative of a good prognosis for the CRC or CRC metastasis.

20 Claims, 13 Drawing Sheets
Specification includes a Sequence Listing.

(56) References Cited

OTHER PUBLICATIONS

Ogino et al., "A Cohort Study of Tumoral LINE-1 Hypomethylation and Prognosis in Colon Cancer," Brief Communications, JNCI, 2008, vol. 100, issue 23, pp. 1734-1738.
Pu, X-X, et al. "Circulating miR-221 directly amplified from plasma is a potential diagnostic and prognostic marker of colorectal cancer and is correlated with p53 expression," Journal of Gastroenterology and Hepatology, 2010, vol. 25, pp. 1674-1680.
Scott et al., Gut, 1993, vol. 34, pp. 289-292.
Slaby, et al., "Altered expression of miR-21, miR-31, miR-143 and miR-145 is related to clinicopathologic features of colorectal cancer," Oncology. 2007;72(5-6):397-402.
Wang, X. et al. "Spreading of Alu Methylation to the Promoter of the MLH1 Gene in Gastrointestinal Cancer", PLoS One, Oct. 2011, vol. 6, Issue 10, e25913, pp. 1-6.
Zhang, Y. et al. "microRNA-320a inhibits tumor invasion by targeting neuropilin 1 and is associated with liver metastasis in colorectal cancer", Oncology Reports, 2012, vol. 27, pp. 685-694. Published online: Nov. 23, 2011.
Zhang, P. et al. "Comprehensive gene and microRNA expression profiling reveals the crucial role of has-let-7i and its target genes in colorectal cancer metastasis", Molecular Biology Reports, 2012, vol. 39, No. 2, pp. 1471-1478. Published online: May 29, 2011.
Cheng, et al., "Circulating Plasma MiR-141 Is a Novel Biomarker for Metastatic Colon Cancer and Predicts Poor Prognosis," PLoS One 6(3):e17745. Doi:10.1371/journal.pone.0017745, (2011).
Database Biosis, [Online], Keun, et al., "Identification of a Novel Metastasis-Specific miRNA Signature in Human Colorectal Cancer," May 1, 2012, XP002692684, retrieved from BIOSIS.

* cited by examiner

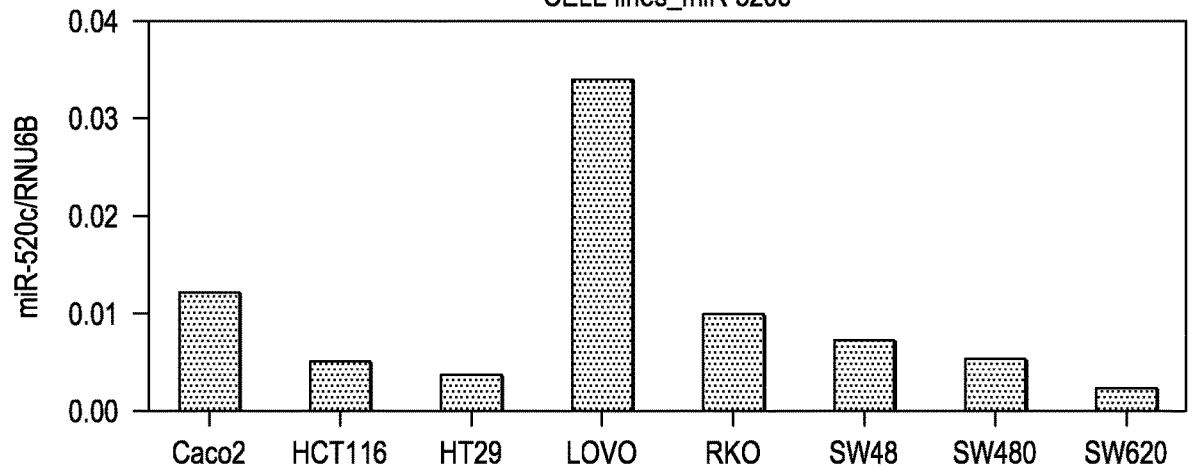
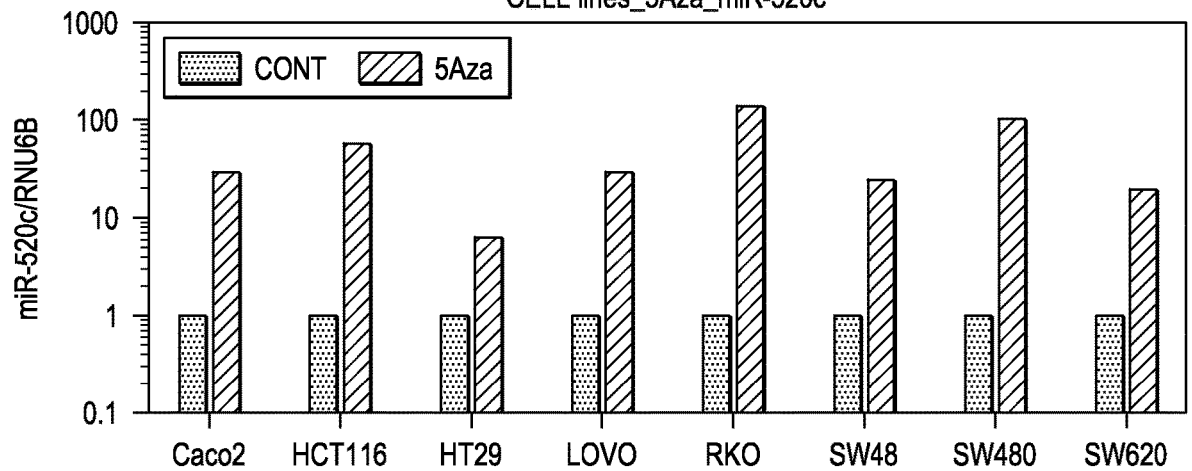

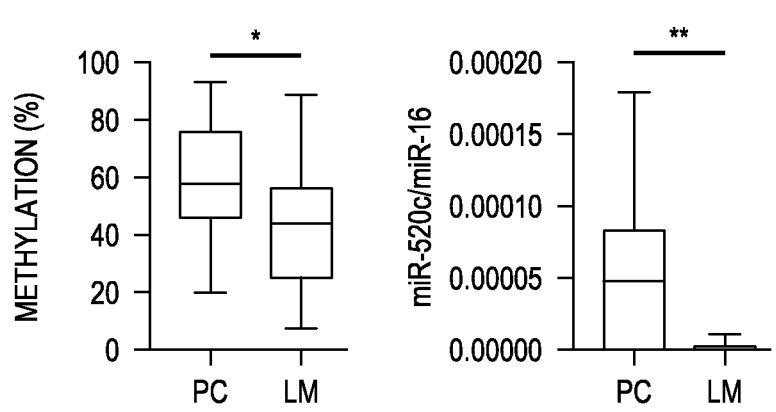
FIG. 8B
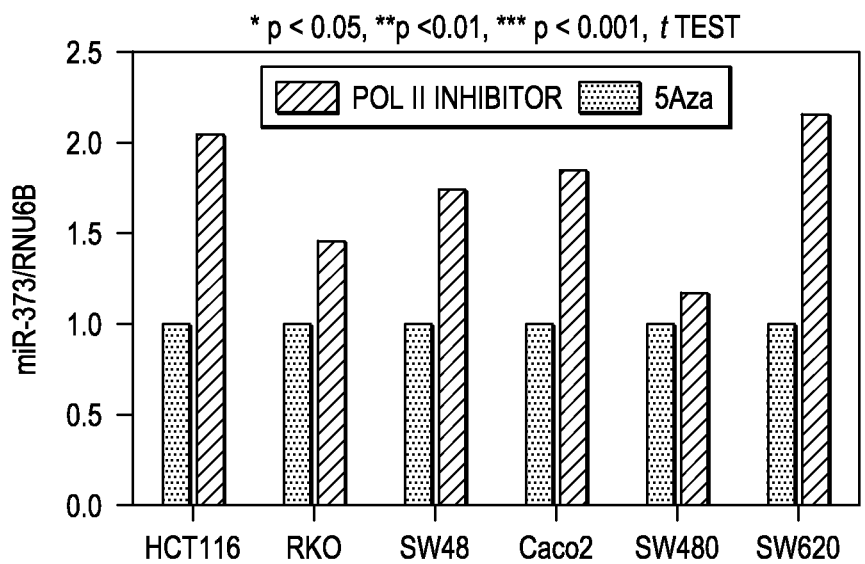
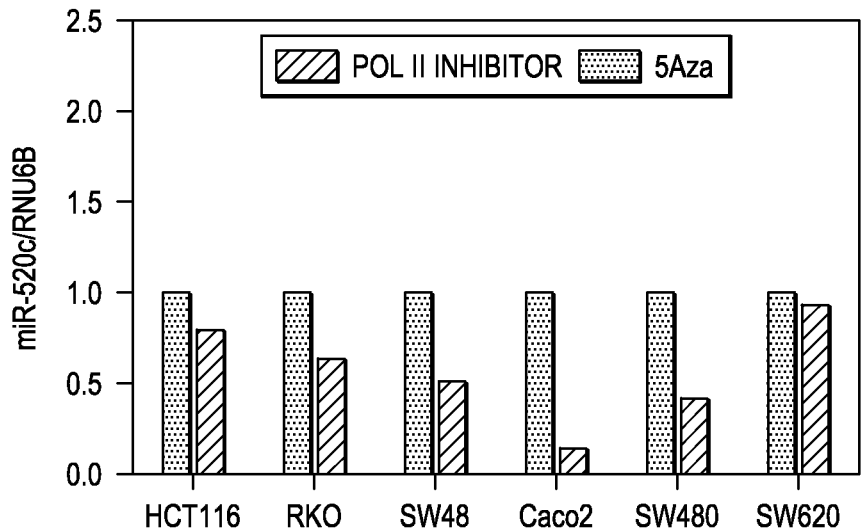
FIG. 9

GOOD PROGNOSIS miRNAs IN LOW EXPRESSION

IDENTIFICATION OF METASTASIS-SPECIFIC MIRNA AND HYPOMETHYLATION SIGNATURES IN HUMAN COLORECTAL CANCER

CROSS REFERENCE TO RELATED APPLICATIONS

This application is a national phase application under 35 USC § 371 of International Application No. PCT/US2012/071455 filed Dec. 21, 2012, which claims priority to U.S. Provisional Application No. 61/579,361 filed Dec. 22, 2011, and U.S. patent application Ser. No. 13/725,402, filed Dec. 21, 2012. The entire contents of each of the above-referenced disclosures is incorporated herein by reference.

STATEMENT OF FEDERALLY FUNDED RESEARCH

This invention was made with U.S. Government support under Contract Nos. RO1 CA72851 and CA129286 awarded by the National Cancer Institute (NCI)/National Institutes of Health (NIH). The government has certain rights in this invention.

TECHNICAL FIELD OF THE INVENTION

The present invention relates in general to the field of cancer detection and diagnosis, and more particularly, to novel metastasis-specific miRNA and hypomethylation signatures in metastatic human colorectal cancer.

BACKGROUND OF THE INVENTION

Without limiting the scope of the invention, its background is described in connection with colorectal cancer detection.

United States Patent Application Publication No. 20110183859, filed by Harris; et al., entitled, Inflammatory Genes and Microrna-21 as Biomarkers for Colon Cancer Prognosis, discloses methods for detecting a more aggressive form of a colon adenocarcinoma in a subject, thereby predicting the prognosis of the subject. The methods taught include determining an inflammatory gene expression signature in the colon adenocarcinoma and/or the adjacent non-cancerous tissue. In some embodiments, the inflammatory genes include, but are not limited to, PRG1, ANXA1, IL-17a, IL-23a FOXP3, HLA-DRA, IL-10, CD68 and IL-12a. In some embodiments, the method further includes detecting expression of microRNA-21 (miR-21) in the colon adenocarcinoma. Altered expression of one or more of the inflammatory genes or miR-21 indicates the prognosis of the subject. Also provided were arrays consisting essentially of probes specific for PRG1, ANXA1, IL-17a, IL-23a, FOXP3, HLA-DRA, IL-10, CD68, IL-12a and miR-21.

International Patent Publication No. WO 2011128900A2, filed by Aviram, et al., entitled, Plasma Based Micro-RNA Biomarkers and Methods for Early Detection of Colorectal Cancer, discloses compositions, methods and kits for diagnosing cancer, specifically the diagnosis of colorectal cancer (CRC). More specifically, the invention provides simple assays, with high sensitivity and specificity for CRC, wherein a panel of microRNA (miRNA) are used as biomarkers. A method is taught for diagnosing metastasis of CRC in a subject is taught in which the expression level of miRs selected from the group consisting of miR566, miR96, miR183, miR194, miR200a, miR200b, miR200c, miR203 and miR429, or combinations thereof, in a biological sample obtained from the subject, wherein a significant elevation in the expression levels of the miRNAs in the biological sample compared to control values indicates that said subject is afflicted with metastasis of CRC. Other biomarkers included hsa-miR-16-2*, hsa-miR-25, hsa-miR-7, hsa-miR-93, hsa-miR-345, hsa-miR-409-3p, hsa-miR-671-3p and hsa-miR-331-3p.

Slaby, et al., Oncology 2007; 72: 397-402, "Altered Expression of miR-21, miR-31, miR-143 and miR-145 is Related to Clinicopathologic Features of Colorectal Cancer," analyzes the expression levels of miR-21, miR-31, miR-143 and miR-145 in 29 primary colorectal carcinomas and 6 non-tumor adjacent tissue specimens were examined by real-time polymerase chain reaction.

Huang, et al., Journal of Digestive Diseases, Volume 10, Issue 3, pages 188-194, August 2009, "MicroRNA expression profile in non-cancerous colonic tissue associated with lymph node metastasis of colon cancer", analyzes MicroRNAs isolated from six frozen non-cancerous surrounding colonic tissues derived from stage II-III colon cancer patients with (n=3) and without (n=3) lymph node metastasis. They compared microRNA expression profiles for six non-cancerous colonic tissues from two colon cancer patient groups; those with confirmed lymph node metastasis, termed the lymph node positive group, and those without detectable lymph node metastasis, termed the lymph node negative group. MicroRNA expression was analyzed with Agilent microarrays containing 723 human microRNA probes and they validated the expression level of differentially expressed microRNA using quantitative real-time PCR analysis, such as, hsa-miR-129*, hsa-miR-137, miR-15b, miR-181b, miR-19 and miR-200c.

SUMMARY OF THE INVENTION

In one embodiment the present invention includes a method for diagnosing or detecting colorectal cancer metastasis in a human subject comprising the steps of: obtaining one or more biological samples from the human subject; determining an Alu repeat methylation level for the one or more biological samples; and comparing the Alu repeat methylation level in the biological sample to an Alu repeat methylation control level from a normal non-cancerous sample, wherein a decrease in the Alu repeat methylation level is indicative of at least one of colorectal cancer disease progression or colorectal cancer metastasis. In one aspect, the biological samples are selected from the group consisting of a tissue sample, a plasma sample, a fecal sample, a cell homogenate, a blood sample, one or more biological fluids, or any combinations thereof. In another aspect, the Alu repeat methylation level is determined by quantitative bisulfite pyrosequencing, thin layer chromatography (TLC), high performance liquid chromatography (HPLC), mass spectrometry (MS), nanopore amperometry, nanopore sequencing, single-molecule, real-time (SM-RT) sequencing, endonuclease digestion, microarrays, matrix-assisted laser desorption ionization time-of-flight (MALDI-TOF) mass spectrometry, and next-generation sequencing. In another aspect, the Alu repeat methylation level is determined by measuring the expression status of miR-520c and miR-373 in the biological sample when compared to a normal non-cancerous sample from the human subject obtained from a human subject that does not have cancer. In another aspect, the non-cancerous sample is from the same patient. In another aspect, the metastatic cancer is a liver metastasis of a colorectal cancer. In another aspect, the method further comprises the steps of: determining an expression level for the one or more biological samples for at least one first marker selected from let-7i, miR-10b, miR-200b, miR-320a, and miR-518d and at least one second marker selected from miR-141, miR-200c, and miR-203; and comparing the expression levels of the first and second markers to the biological sample, wherein a decrease in the level of expression of the at least one first marker and an increase in the level of expression of the second marker when compared to the level of expression in a normal tissue sample is indicative of colorectal cancer metastasis. In another aspect, the method further comprises the steps of treating the colorectal cancer with a therapeutic agent, obtaining one or more patient samples and determining if there has been a change in the expression of the one or more microRNAs, wherein a change in expression is indicative of colorectal cancer metastasis.

Another embodiment of the present invention includes a kit for determining a detection, prediction, or prognosis for colorectal cancer in a human subject comprising: a biomarker detecting reagent for measuring at least one first marker selected from let-7i, miR-10b, miR-320a, and miR-221 in a sample obtained from the human subject; and instructions for the use of the biomarker detecting reagent in the prognosis of colorectal cancer metastasis, wherein the instructions comprise providing step-by-step directions to compare the level of expression of let-7i, miR-10b, miR-320a, and miR-221 in the sample with the level of expression of let-7i, miR-10b, miR-320a, and miR-221 from normal colorectal tissue, wherein high expression of at least on of let-7i or miR-320a is indicative of a good prognosis for the colorectal cancer, while the low expression of at least one of miR-10b or miR-221 is indicative of a good prognosis for the colorectal cancer or colorectal cancer metastasis. In one aspect, the biological samples are selected from the group consisting of a tissue sample, a plasma sample, a fecal sample, a cell homogenate, a blood sample, one or more biological fluids, or any combinations thereof. In another aspect, the level of expression of let-7i, miR-10b and miR-320a in primary colorectal cancer is prognostic of distant metastasis. In another aspect, the level of expression of let-7i, miR-10b correlated with the TNM stage. In another aspect, a high level of expression of let-7i indicates a good prognosis for colorectal cancer survival. In another aspect, a low level of expression of let-7i indicates a poor prognosis for colorectal cancer survival. In another aspect, a high level of expression of at least one of let-7i or miR-320a is predictive of less cancer metastasis. In another aspect, a low level of expression of at least one of miR-10b or miR-221 is predictive of less cancer metastasis. In another aspect, the metastatic cancer is a liver metastasis of a colorectal cancer. In another aspect, the level of expression is determined by digital color-coded barcode technology analysis, microarray expression profiling, PCR, reverse transcriptase PCR, reverse transcriptase real-time PCR, quantitative real-time PCR, end-point PCR, multiplex end-point PCR, cold PCR, ice-cold PCR, mass spectrometry, or nucleic acid sequencing. In another aspect, the method further comprises the detection of miR-122, wherein an increase in miR-122 is correlated with liver metastasis. In another aspect, the method further comprises the detection of one or more microRNAs selected from miR-199b-5p, miR-484, miR-490-3p, miR-520e, miR-337-5p, miR-485-39, miR-145, miR-144, miR-216a, miR-92b, miR-365, miR-708 or miR-143, wherein a decrease in expression is correlated with liver metastasis from a primary colorectal tumor. In another aspect, the method further comprises the steps of treating the colorectal cancer with a therapeutic agent, obtaining one or more patient samples and determining if there has been a change in the expression of the one or more microRNAs, wherein a change in expression is indicative of colorectal cancer metastasis.

Another embodiment of the present invention includes a biomarker for detecting colorectal cancer metastasis in a human subject comprising: a biomarker to determine a methylation level of an Alu repeat, wherein a lower methylation level of the Alu repeat is indicative of colorectal cancer and colorectal cancer metastasis in the human subject. In one aspect, the biomarker further comprises at least one first marker selected from let-7i, miR-10b, miR-200b, miR-320a, and miR-518d and at least one second marker selected from miR-141, miR-200c, and miR-203.

Yet another embodiment of the present invention includes a kit for determining colorectal cancer metastasis in a human subject comprising: a biomarker detecting reagent for measuring an Alu repeat methylation level in a sample obtained from the human subject; and instructions for the use of the biomarker detecting reagent in diagnosing the presence of colorectal cancer metastasis, wherein the instructions comprise providing step-by-step directions to compare the Alu repeat methylation level in the sample with an Alu repeat methylation level from normal colorectal tissue, wherein a decrease in Alu repeat methylation is indicative of colorectal cancer and colorectal cancer metastasis. In one aspect, the sample is selected from the group consisting of a tissue sample, a fecal sample, a plasma sample, a cell homogenate, a blood sample, one or more biological fluids, or any combinations thereof. In another aspect, the Alu repeat methylation level is determined by measuring the expression status of miR-520c and miR-373 in the biological sample when compared to a normal non-cancerous sample from the human subject. In another aspect, the metastatic cancer is a liver metastasis of a colorectal cancer. In another aspect, the kit further comprises reagents to determine the level of expression of at least one first marker selected from let-7i, miR-10b, miR-200b, miR-320a, and miR-518d and at least one second marker selected from miR-141, miR-200c, and miR-203.

Yet another embodiment of the present invention includes a method for selecting a cancer therapy for a suspect diagnosed with colorectal cancer metastasis, the method comprising the steps of: determining a methylation level of an Alu repeat in a biological sample suspected of being a colorectal cancer metastasis, wherein a decrease in the methylation level of the Alu repeat as compared to a non-cancerous colorectal tissue is indicative of colorectal cancer and colorectal cancer metastasis; and selecting the cancer therapy based on the determination of the presence of colorectal cancer metastasis in the subject.

Another embodiment of the present invention includes a method of performing a clinical trial to evaluate a candidate drug believed to be useful in treating colorectal cancer metastasis, the method comprising: (a) determining the presence of colorectal cancer metastasis by a method comprising the steps of: determining an overall Alu repeat methylation level in one or more cells obtained from a biological sample of the subject, wherein a lower overall Alu repeat methylation level compared to a reference control is indicative of colorectal cancer and colorectal cancer metastasis; (b) administering a candidate drug to a first subset of the patients, and a placebo to a second subset of the patients; a comparable drug to a second subset of the patients; or a drug combination of the candidate drug and another active agent to a second subset of patients; (c) repeating step (a)

after the administration of the candidate drug or the placebo, the comparable drug or the drug combination; and (d) monitoring a change in the overall Alu repeat methylation level as compared to any reduction occurring in the second subset of patients, wherein a statistically significant reduction in cancer metastasis indicates that the candidate drug is useful in treating said disease state.

In yet another embodiment the present invention includes a method of performing a clinical trial to evaluate a candidate drug believed to be useful in treating colorectal cancer metastasis, the method comprising: (a) determining a level of expression of at least one of let-7i, miR-10b, miR-320a, or miR-221 in the sample from the one or more biological samples in one or more cells obtained from a biological sample of the subject, wherein a lower overall expression level of the first marker and a higher expression level in the second marker, when compared to a reference control, is indicative of colorectal cancer metastasis; (b) administering a candidate drug to a first subset of the patients, and a placebo to a second subset of the patients; a comparable drug to a second subset of the patients; or a drug combination of the candidate drug and another active agent to a second subset of patients; (c) repeating step (a) after the administration of the candidate drug or the placebo, the comparable drug or the drug combination; and (d) monitoring a change in the overall expression level of the at least one of let-7i, miR-10b, miR-320a, or miR-221 as compared to any change in the second subset of patients, wherein a statistically significant decrease in the first marker and an increase in the second marker indicates that the candidate drug is useful in treating the disease state.

Yet another embodiment of the present invention includes a method for detecting colorectal cancer metastasis in a human subject comprising the steps of: identifying the human subject suspected of suffering from a colorectal cancer metastasis; obtaining one or more biological samples suspected of being metastatic from the human subject; determining an Alu repeat methylation level for the one or more biological samples; and comparing the Alu repeat methylation level from the human subject to an Alu repeat methylation level from normal colorectal tissue, wherein a lower degree of methylation in the Alu repeat level from the human subject is indicative of colorectal cancer and colorectal cancer metastasis. In one aspect, the biological samples are selected from the group consisting of a tissue sample, a plasma sample, a fecal sample, a cell homogenate, a blood sample, one or more biological fluids, or any combinations thereof. In another aspect, the Alu repeat methylation level is determined by quantitative bisulfite pyrosequencing, thin layer chromatography (TLC), high performance liquid chromatography (HPLC), mass spectrometry (MS), nanopore amperometry, nanopore sequencing, single-molecule, real-time (SM-RT) sequencing, endonuclease digestion, microarrays, matrix-assisted laser desorption ionization time-of-flight (MALDI-TOF) mass spectrometry, and next-generation sequencing. In another aspect, the Alu repeat methylation level is determined by measuring the expression status of miR-520c and miR-373 in the biological sample when compared to a normal non-cancerous sample from the human subject. In another aspect, the metastatic cancer is a liver metastasis of a colorectal cancer. In another aspect, the method further comprises the steps of: determining an expression level for the one or more biological samples for at least one first marker selected from let-7i, miR-10b, miR-200b, miR-320a, and miR-518d and at least one second marker selected from miR-141, miR-200c, and miR-203; and comparing the expression levels of the markers to a colorectal sample that is normal control level, wherein a decrease in the level of expression of the at least one first marker and an increase in the level of expression of the second marker is also indicative of colorectal cancer metastasis.

Another embodiment of the present invention includes a method for diagnosis, prediction, or prognosis of colorectal cancer in a human subject comprising the steps of: obtaining one or more biological samples from the human subject; determining a level of expression of let-7i, miR-10b, miR-320a, and miR-221 in the sample from the one or more biological samples; and comparing the level of expression of let-7i, miR-10b, miR-320a, and miR-221 in the sample with the level of expression of let-7i, miR-10b, miR-320a, and miR-221 from normal colorectal tissue, wherein high expression of at least on of let-7i or miR-320a is indicative of a good prognosis for the colorectal cancer, while the low expression of at least one of miR-10b or miR-221 is indicative of a good prognosis for the colorectal cancer or colorectal cancer metastasis. In one aspect, the biological samples are selected from the group consisting of a tissue sample, a plasma sample, a fecal sample, a cell homogenate, a blood sample, one or more biological fluids, or any combinations thereof. In another aspect, the level of expression of let-7i, miR-10b and miR-320a in primary colorectal cancer is prognostic of distant metastasis. In another aspect, the level of expression of let-7i, miR-10b correlated with the TNM colorectal cancer stage. In another aspect, a high level of expression of let-7i indicates a good prognosis for colorectal cancer survival. In another aspect, a low level of expression of let-7i indicates a poor prognosis for colorectal cancer survival. In another aspect, a high level of expression of at least one of let-7i or miR-320a is predictive of less cancer metastasis. In another aspect, a low level of expression of at least one of miR-10b or miR-221 is predictive of less cancer metastasis. In another aspect, the metastatic cancer is a liver metastasis of a colorectal cancer. In another aspect, the level of expression is determined by digital color-coded barcode technology analysis, microarray expression profiling, PCR, reverse transcriptase PCR, reverse transcriptase real-time PCR, quantitative real-time PCR, end-point PCR, multiplex end-point PCR, cold PCR, ice-cold PCR, mass spectrometry, or nucleic acid sequencing. In another aspect, the method further comprises the detection of miR-122, wherein an increase in miR-122 is correlated with liver metastasis. In another aspect, the method further comprises the detection of one or more microRNAs selected from miR-199b-5p, miR-484, miR-490-3p, miR-520e, miR-337-5p, miR-485-39, miR-145, miR-144, miR-216a, miR-92b, miR-365, miR-708 or miR-143, wherein a decrease in expression is correlated with liver metastasis from a primary colorectal tumor.

Yet another embodiment of the present invention includes a method for diagnosing or detecting colorectal cancer metastasis in a human subject comprising the steps of: obtaining one or more biological samples from the human subject suspected of comprising a metastatic cancer; determining an expression level for the one or more biological samples for at least one first marker selected from let-7i, miR-10b, miR-200b, miR-320a, and miR-518d and at least one second marker selected from miR-141, miR-200c, and miR-203; and comparing the expression levels of the markers to a colorectal sample that is normal control level, wherein a decrease in the level of expression of the at least one first marker and an increase in the level of expression of the second marker is indicative of colorectal cancer metastasis. In one aspect, the biological samples are selected from the group consisting of a tissue sample, a plasma sample, a fecal sample, a cell homogenate, a blood sample, one or more biological fluids, or any combinations thereof. In another aspect, the expression level of 2, 3, 4, or 5 of the first marker microRNAs are downregulated. In another aspect, the expression level of 2 or 3 of the second marker microRNAs are upregulated. In another aspect, the expression level of the first and second markers is measured by microarray expression profiling, PCR, reverse transcriptase PCR, reverse transcriptase real-time PCR, quantitative real-time PCR, end-point PCR, multiplex end-point PCR, cold PCR, ice-cold PCR, mass spectrometry, or nucleic acid sequencing. In another aspect, the metastatic cancer is a liver metastasis of a colorectal cancer. In another aspect, the method further comprises the step of determining an Alu repeat methylation level for the one or more biological samples; and comparing the Alu repeat methylation level to an Alu repeat methylation level from normal colorectal tissue, wherein a decrease in the Alu repeat methylation level is also indicative of colorectal cancer and colorectal cancer metastasis.

Yet another embodiment of the present invention also includes a biomarker for colorectal metastasis that comprises at least one first marker selected from microRNAs: let-7i, miR-10b, miR-200b, miR-320a, and miR-518d; and at least one second marker selected from microRNAs: miR-141, miR-200c, and miR-203, wherein a change in the overall expression of the one or more first and the second marker a sample obtained from a patient is indicative of colorectal metastasis when compared to the overall expression of the first and second marker expression in normal colorectal neoplasia cells or colorectal neoplasia cells obtained at an earlier timepoint from the same patient. In another aspect, the first markers are underexpressed in metastatic cancer and are selected from 2, 3, 4, or 5 of the microRNAs. In another aspect, 2 or 3 of the second marker microRNAs are overexpressed in metastatic cancer. In another aspect, the biomarker further comprises an Alu repeat methylation level of the sample and an Alu repeat methylation control level, wherein a lower degree of the Alu repeat methylation level is also indicative of colorectal cancer and colorectal cancer metastasis.

Yet another embodiment of the present invention includes a kit for determining colorectal cancer metastasis in a human subject comprising: a biomarker detecting reagent for measuring at least one first marker selected from microRNAs: let-7i, miR-10b, miR-200b, miR-320a, and miR-518d; and at least one second marker selected from microRNAs: miR-141, miR-200c, and miR-203 level in a sample; and instructions for the use of the biomarker detecting reagent in diagnosing the presence of colorectal cancer metastasis, wherein the instructions comprise providing step-by-step directions to compare the expression level for the first and second markers in the sample with a normal colorectal tissue which comprises a control level. In another aspect, the sample is selected from the group consisting of a tissue sample, a fecal sample, a plasma sample, a cell homogenate, a blood sample, one or more biological fluids, or any combinations thereof. In another aspect, the normal colorectal tissue control level is obtained from a biological sample obtained from a healthy subject, wherein the healthy subject is a human subject not suffering from cancer metastasis or non-cancerous tissue from the same patient. In another aspect, the kit further comprises an Alu repeat methylation detecting reagent to determine the Alu repeat methylation level of the sample and an Alu repeat methylation control level, wherein a lower degree of the Alu repeat methylation level is also indicative of colorectal cancer and colorectal cancer metastasis. In another aspect, the metastatic cancer is a liver metastasis of a colorectal cancer.

Another embodiment of the present invention includes a method of performing a clinical trial to evaluate a candidate drug believed to be useful in treating colorectal cancer metastasis, the method comprising: (a) determining the presence of colorectal cancer metastasis by a method comprising the steps of: determining an overall level of expression of at least one first marker selected from microRNAs: let-7i, miR-10b, miR-200b, miR-320a, and miR-518d; and at least one second marker selected from microRNAs: miR-141, miR-200c, and miR-203 in one or more cells obtained from a biological sample of the subject, wherein a lower overall expression level of the first marker and a higher expression level in the second marker, when compared to a reference control, is indicative of colorectal cancer metastasis; (b) administering a candidate drug to a first subset of the patients, and a placebo to a second subset of the patients; a comparable drug to a second subset of the patients; or a drug combination of the candidate drug and another active agent to a second subset of patients; (c) repeating step (a) after the administration of the candidate drug or the placebo, the comparable drug or the drug combination; and (d) monitoring a change in the overall expression level of the first and second markers as compared to any change in the second subset of patients, wherein a statistically significant decrease in the first marker and an increase in the second marker indicates that the candidate drug is useful in treating the disease state.

Yet another embodiment of the present invention includes a method for detecting colorectal cancer metastasis in a human subject comprising the steps of: identifying the human subject suspected of suffering from a colorectal cancer; obtaining one or more biological samples from the human subject; determining the level of expression of at least one first marker selected from microRNAs: let-7i, miR-10b, miR-200b, miR-320a, and miR-518d; and at least one second marker selected from microRNAs: miR-141, miR-200c, and miR-203 for the one or more biological samples; and comparing the expression level of the first and second markers to the expression level of the first and second markers in normal tissues, wherein a decrease in the expression level of the first marker and an increase in the expression level of the second marker as compared to normal tissue is indicative of colorectal cancer metastasis. In one aspect, the biological samples are selected from the group consisting of a tissue sample, a plasma sample, a fecal sample, a cell homogenate, a blood sample, one or more biological fluids, or any combinations thereof. In another aspect, the expression level of 2, 3, 4, or 5 of the first marker microRNAs are downregulated. In another aspect, the expression level of 2 or 3 of the second markers microRNAs are upregulated. In another aspect, the expression level of the first and second markers is measured by microarray expression profiling, PCR, reverse transcriptase PCR, reverse transcriptase real-time PCR, quantitative real-time PCR, end-point PCR, multiplex end-point PCR, cold PCR, ice-cold PCR, mass spectrometry, or nucleic acid sequencing. In another aspect, the metastatic cancer is a liver metastasis of a colorectal cancer. In another aspect, the method further comprises the step of determining an Alu repeat methylation level for the one or more biological samples; and comparing the Alu repeat methylation level to an Alu repeat methylation control level, wherein a lower degree of the Alu repeat methylation level is also indicative of colorectal cancer and colorectal cancer metastasis. Yet another embodiment of the present invention includes a method of diagnosing or providing a prognosis for colorectal cancer metastasis, the method comprising the steps of: obtaining a biological sample from a human subject suspected of or having colorectal cancer metastasis; detecting in the biological sample altered expression for an Alu repeat methylation level for the one or more biological samples, wherein a decrease in the Alu repeat methylation level is indicative of at least one of colorectal cancer disease progression or colorectal cancer metastasis; and providing a diagnosis or prognosis for colorectal cancer metastasis. Another embodiment includes a method of diagnosing or providing a prognosis for colorectal cancer metastasis, the method comprising the steps of: obtaining a biological sample from a human subject suspected of or having colorectal cancer metastasis; detecting in the biological sample altered expression (over or under expression of at least 50% compared to a subject without colorectal cancer metastasis) of let-7i, miR-10b, miR-320a, and miR-221, wherein high expression of at least one of let-7i or miR-320a is indicative of a good prognosis for the colorectal cancer, while the low expression of at least one of miR-10b or miR-221 is indicative of a good prognosis for the colorectal cancer or colorectal cancer metastasis; and providing a diagnosis or prognosis for colorectal cancer metastasis.

The high risk patient with poor prognosis is a candidate for adjunctive therapy. Following surgical resection of the tumor, the patient is administered chemotherapy as the adjunctive therapy. An appropriate chemotherapy agent and treatment regimen can be determined by one of skill in the art. Chemotherapy protocols for treating patients with colon adenocarcinoma are well known in the art (see, for example, Lembersky et al., J. Clin. Oncol. 24:2059, 2006; and Haller et al., J. Clin. Oncol. 23:8671, 2005, herein incorporated by reference). A high risk colon adenocarcinoma patient is administered 5-fluorouracil (5-FU) in combination with leucovorin. 5-FU (500 mg/m2) is administered by intravenous bolus injection one hour after the start of leucovorin administration. Leucovorin (500 mg/m2) is administered intravenously over the course of two hours. This treatment is administered weekly for six weeks, followed by a two week break in treatment. The 8-week treatment cycle is repeated for a total of 3 or 4 cycles.

BRIEF DESCRIPTION OF THE DRAWINGS

For a more complete understanding of the features and advantages of the present invention, reference is now made to the detailed description of the invention along with the accompanying figures and in which:

FIG. 6A is an analysis of the expression of miR-520c. All cell lines showed low level of miR-520c expression, except Lovo cell.

FIG. 6B shows that the expression of miR-520c was induced by a demethylating agent. This data indicates that miR-520c expression is regulated by Alu methylation in promoter region.

FIG. 8B shows that Alu hypomethylation did not correlate with miR-520c expression in LM.

FIG. 9 shows that an RNA pol II inhibitor did not suppress activation of miR-373, but inhibited the expression of miR-520c.

DETAILED DESCRIPTION OF THE INVENTION

Figure 1:
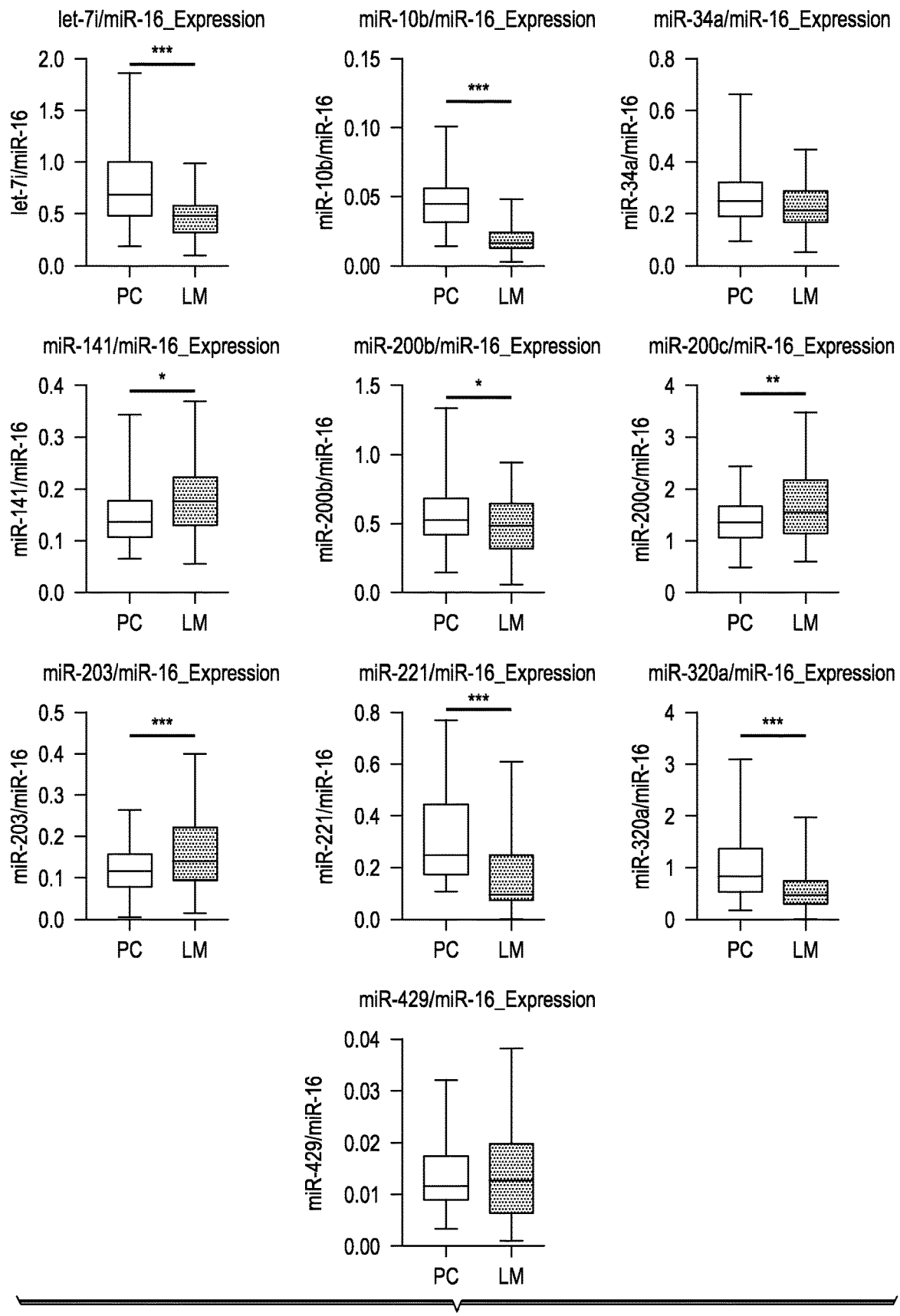
FIG. 1 shows the expression analysis of metastasis predictive microRNAs expression comparing Primary Colorectal (PC) cancer microRNA expression compared to colorectal cancer (CRC) liver metastasis (LM) microRNA expression.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes biomarkers and methods for detecting Colorectal Cancer (CRC) metastasis and exploring curative target of metastasized CRC, including but not limited to cancer research, cancer screening, diagnosis of metastasis, planning of cancer treatment and molecular target of anti-cancer drug.

As used herein, the term "colorectal cancer" includes the well-accepted medical definition that defines colorectal cancer as a medical condition characterized by cancer of cells of the intestinal tract below the small intestine (i.e., the large intestine (colon), including the cecum, ascending colon, transverse colon, descending colon, sigmoid colon, and rectum). Additionally, as used herein, the term "colorectal cancer" also further includes medical conditions, which are characterized by cancer of cells of the duodenum and small intestine (jejunum and ileum).

As used herein, the term "tissue sample" (the term "tissue" is used interchangeably with the term "tissue sample") includes any material composed of one or more cells, either individual or in complex with any matrix obtained from a patient. The definition includes any biological or organic material and any cellular subportion, product or by-product thereof. The definition of "tissue sample" should be understood to include without limitation colorectal tissue samples, tissues suspected of including colorectal cancer cells, blood components, and even fecal matter or fluids that includes colorectal cells. Also included within the definition of "tissue" for purposes of this invention are certain defined acellular structures such as dermal layers of epithelium that have a cellular origin but are no longer characterized as cellular. The term "stool" or "feces" as used herein is a clinical term that refers to feces obtained from a mammal such as a human.

As used herein, the term "biological fluid" refers to a fluid containing cells and compounds of biological origin, and may include blood, stool or feces, lymph, urine, serum, pus, saliva, seminal fluid, tears, urine, bladder washings, colon washings, sputum or fluids from the respiratory, alimentary, circulatory, or other body systems. For the purposes of the present invention the "biological fluids", the nucleic acids containing the biomarkers may be present in a circulating cell or may be present in cell-free circulating DNA or RNA.

As used herein, the term "gene" refers to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated. The term "allele" or "allelic form" refers to an alternative version of a gene encoding the same functional protein but containing differences in nucleotide sequence relative to another version of the same gene.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

As used herein, a "biomarker" refers to a molecular indicator that is associated with a particular pathological or physiological state. The "biomarker" as used herein is a molecular indicator for cancer, more specifically an indicator for primary CRCs and distant metastasis of primary CRCs. Examples of "biomarkers" include let-7i, miR-10b, miR-30b, miR-34a, miR-141, miR-200b, miR-200c, miR-203, miR-221, miR-320a, miR-373, miR-429, miR-518d, and miR-520c.

As used herein, the term "statistically significant" refers to differences between the groups studied, relates to condition when using the appropriate statistical analysis (e.g. Chi-square test, t-test) the probability of the groups being the same is less than 5%, e.g. $p<0.05$. In other words, the probability of obtaining the same results on a completely random basis is less than 5 out of 100 attempts. The skilled artisan will recognize that there will be variability in certain measurements, for example, the level of mir-148a expression was determined by normalizing the expression to, e.g., miR-16, thus, the number 0.069-fold is not a definitive number. As a general matter, when the terms "higher" or "lower" are used to indicate the level of expression of a MiR, this indicates a statistically "higher" or "lower" level of expression for that same marker (e.g., miR-148a) in a CRC sample versus normal mucosa. As demonstrated in the figures disclosed herein (where expression is generally shown as a range), the skilled artisan can determine the statistical significance of the measured biomarker in relation to that expressed in normal colorectal tissue from the same patient. Thus, the cut-off value can be determined in the context of the same patient, thus yielding a statistically significant measurement for an increase or decrease in expression. It is also possible to measure invariant markers from CRC, e.g., miR-16, that can also be used to normalize levels of expression.

As used herein, the term "kit" or "testing kit" denotes combinations of reagents and adjuvants required for an analysis. Although a test kit consists in most cases of several units, one-piece analysis elements are also available, which must likewise be regarded as testing kits.

As used herein, the term "TNM" refers to the internationally recognized TNM classification of malignant tumors developed and maintained by the International Union Against Cancer, which has been adopted by the American Joint Committee on Cancer (AJCC) and the International Federation of Gynecology and Obstetrics (FIGO). T refers to the size or direct extent of the primary tumor; N to the degree of spread to regional lymph nodes, and M to the presence of metastasis.

The present invention includes the identification and use of miRNA biomarkers (let-7i, miR-10b, miR-30b, miR-34a, miR-141, miR-200b, miR-200c, miR-203, miR-221, miR-320a, miR-373, miR-429, miR-518d, and miR-520c) that have been found to be very specific for detecting liver metastasized CRC. Most of the existing cancer metastasis biomarkers are developed through comparison between primary tissues with metastasis and without metastasis. In contrast, the present invention is based on a detailed analysis and discovery that certain miRNA biomarkers were identified by direct comparison between primary CRC and matching liver metastasis tissues, rather than a comparison to primary tissues. These biomarkers were validated using tissue sample miRNAs expression, but also using serum samples of CRC patients with distant metastasis. Furthermore, it was found that Alu repetitive element was hypomethylated in distant metastasized tissues compared to primary CRC, which can regulate the expression of some of the miRNA biomarkers (miR-30b, miR-373, miR-518d, and miR-520c) of the present invention. DNA modification is biologically and chemically stable than RNA transcription. Thus, the miRNA biomarkers of the present invention are more accurate and specific compared to biomarkers developed using just primary cancer tissues.

The present invention has several advantages when compared to existing miRNA biomarkers. First, the miRNAs biomarkers of the present invention are metastasis specific biomarkers because they are derived from the direct comparison between primary CRC and matching liver metastasis tissues. Second, the miRNAs biomarkers of the present invention are more specific for the detection of CRC metastasis, as validated using miRNAs expression of serum samples from CRC patients with and without distant metastasis. Third, the miRNAs biomarkers of the present invention can be applied to detect any diseases which related with global hypomethylation, as it was also found that hypomethylation (decrease of methylation) of Alu repetitive sequence in distant metastasis tissue compared to primary CRC tissue, which can regulate Alu sequence downstream located miRNAs expression (miR-30b, miR-373, miR-518d, and miR-520c).

Materials and Methods. A commercially available kit for miRNA extraction from cell lines, Formalin-Fixed, Paraffin-Embedded (FFPE) tissue, and human serum samples with some modifications. To compare miRNAs expression status between primary CRC and distant metastasized CRC, we have analyzed expression of fourteen metastasis-related miRNAs (let-7i, miR-10b, miR-30b, miR-34a, miR-141, miR-200b, miR-200c, miR-203, miR-221, miR-320a, miR-373, miR-429, miR-518d, and miR-520c) in matched primary colorectal cancer and corresponding liver metastasis tissues from 59 patients. MicroRNA expression levels were determined by quantitative real-time PCR (qRT-PCR) and the data were normalized relative to miR-16 expression. Second, we have also investigated global Alu methylation and local Alu methylation status by quantitative pyrosequencing analysis in matched primary colorectal cancer and corresponding liver metastasis tissues. The skilled artisan will recognize, however, that many different methods for determining methylation can be used with the present invention, e.g., thin layer chromatography (TLC), high performance liquid chromatography (HPLC), mass spectrometry (MS), nanopore amperometry, nanopore sequencing, single-molecule, real-time (SM-RT) sequencing, endonuclease digestion, microarrays, matrix-assisted laser desorption ionization time-of-flight (MALDI-TOF) mass spectrometry, and next-generation sequencing (Laird, Peter W., "Principles and Challenges of Genomewide DNA Methylation Analysis," Nature Review Genetics, Vol. 11, March 2010, pgs 191-203, relevant portions incorporated herein by reference).

The present invention may include the use of digital color-coded barcode technology analysis (e.g., NANOSTRING® technology (such as the nCounter Analysis System, NanoString Technologies, Inc., Seattle, Wash.). The NANOSTRING® protocol includes the following steps: (1) Hybridization: two ~50 base probes per mRNA that hybridize in solution, a reporter probe that carries the signal, while a capture probe allows the complex to be immobilized for data collection. (2) Purification and Immobilization: following hybridization, excess probes are removed and the probe/target complexes are aligned and immobilized in, e.g., an nCounter Cartridge; and (3) Data is collected from the sample cartridges, which can be placed in the digital analyzer instrument for data acquisition using color codes on the surface of the cartridge that are counted and tabulated for each target molecule.

Cell lines and 5-aza-2-deoxy-cytidine treatment. Seven CRC cell lines, HCT116, RKO, SW48, Caco-2, HT29, SW480, and SW620 were obtained from the American Type Culture Collection (ATCC, Rockville, Md.). Cell lines were treated with 2.5 µM 5-Aza-2'-deoxycytidine (5-aza-dC; Sigma-Aldrich) for 72 hours, and fresh medium containing 5-aza-dC was replaced every 24 hours.

Tissue specimens. A total of 59 formalin-fixed, paraffin-embedded (FFPE) matched corresponding normal cololectal mucosa (NM), primary CRC tissues (PC), and liver metastasis tissues (LM) were enrolled in this study. Written informed consent was obtained from all patients and the study was approved by the institutional review boards of all participating institutions. Careful microdissection was performed in order to enrich for tumor cells.

Isolation of RNA and DNA. Total RNA (including miR-NAs) from CRC cell lines was extracted using miRNeasy® Mini Kits (Qiagen). For RNA extraction from FFPE specimens, a Total Nucleic Acid Isolation Kit for FFPE tissues (Ambion, Austin, Tex., USA) was used according to the manufacturer's instructions. DNA was extracted from CRC cell lines using a QIAamp® DNA Mini Kit (Qiagen) and from FFPE specimens using a QIAamp® DNA FFPE Tissue Kit (Qiagen).

miRNA expression analysis. Expression of fourteen metastasis-related miRNAs (let-7i, miR-10b, miR-30b, miR-34a, miR-141, miR-200b, miR-200c, miR-203, miR-221, miR-320a, miR-373, miR-429, miR-518d, and miR-520c) was analyzed using TaqMan miRNA assays (Applied Biosystems Inc., Foster City, Calif.). Expression of RNU6B (Applied Biosystems Inc., Foster City, Calif.) and miR-16 were used as endogenous controls for cell lines and FFPE tissues, respectively.

DNA methylation analysis. Methylation levels of repetitive sequences (global Alu and local Alu) were analyzed by quantitative bisulfite pyrosequencing using the PSQ HS 96A pyrosequencing system (Qiagen) following bisulfite modification of genomic DNA using EZ DNA methylation Gold Kits (Zymo Research), as described previously.

Statistical analysis. Data were analyzed with GraphPad Prism 5.0 software. To evaluate significant differences between two matched pair groups of samples, paired t-tests was used, whereas the difference between two independent groups of samples was analyzed using the Mann-Whitney U test.

Additional materials and methods. CRC Cell line: CACO2, HCT116, RKO, SW48, SW480, and SW620. Tissue specimens: A total of 59 formalin-fixed, paraffin-embedded (FFPE) primary CRC tissues and corresponding liver metastasis tissues were analyzed. 5-Aza-2'-deoxycytidine (5-aza-dC) treatment: CRC cell lines were treated with 2.5 µM 5-aza-dC for 72 hours. α-amanitin treatment: CRC cell lines were treated with 50 µg/ml α-amanitin, a RNA pol II inhibitor, for 7 hours. Methylation analysis: Methylation levels were analyzed by bisulfite pyrosequencing for quantitative methylation analysis using PSQ HS 96A pyrosequencing system (Qiagen) on bisulfite modified genomic DNA template. microRNAs expression analysis: Expression of miR-373 and miR-520c was analyzed using TaqMan miRNA assays.

FIG. 1 shows a metastasis predictive microRNAs expression colorectal cancer (CRC). Briefly, all 10 metastasis predictive candidate miRNAs expression status in matched corresponding primary CRC (PC) and liver metastasized CRC (LM) human tissues by qRT-PCR. Five miRNAs (let7i, miR-10b, miR-200b, miR-221, and miR-320) were significantly down-regulated in LM compared to PC. On the contrary, three miRNAs (miR-141, miR-200c, and miR-203) were significantly up-regulated in LM compared to PC.

Figure 2:
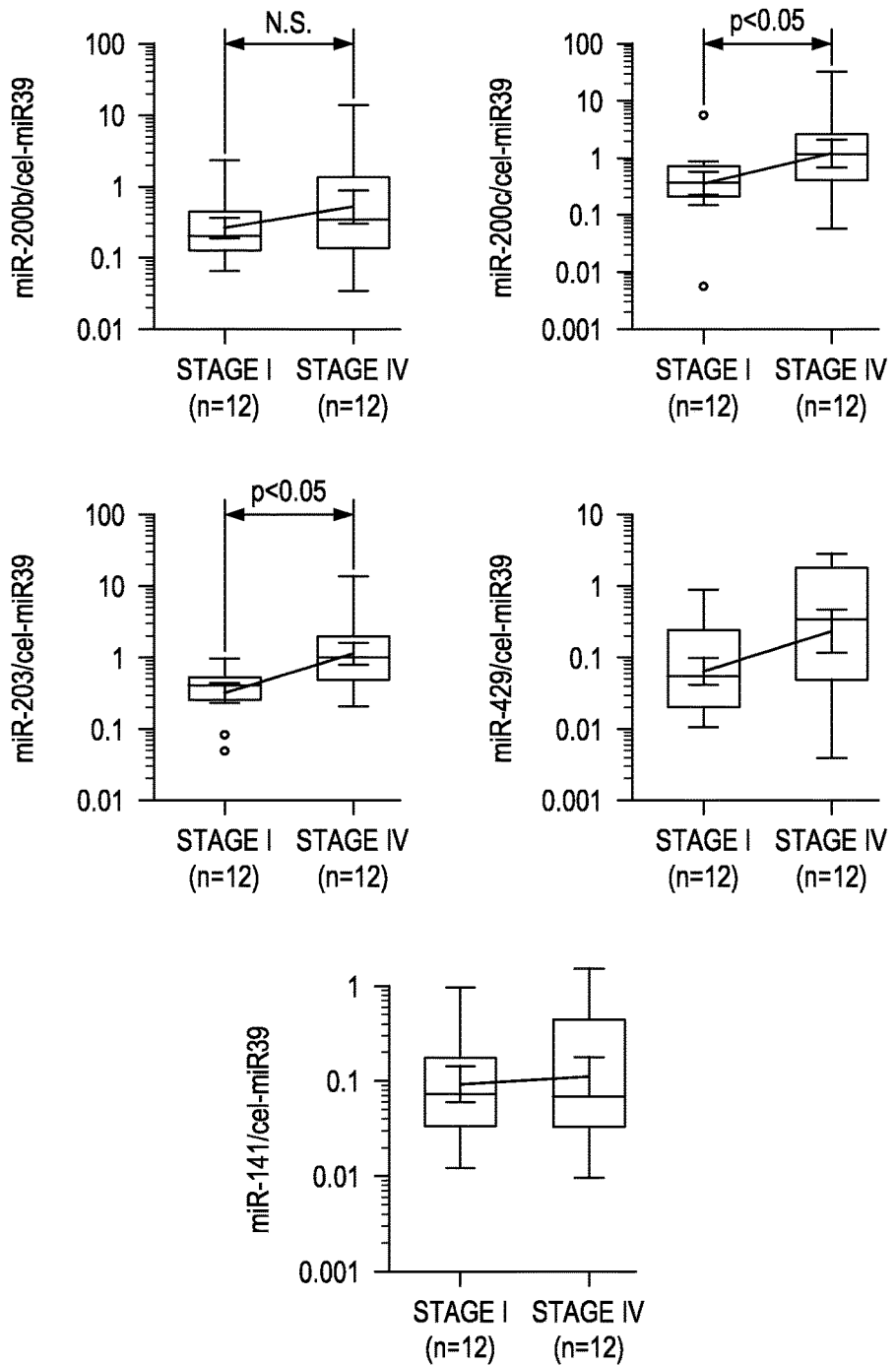
FIG. 2 is an analysis of the expression of the miR-200 family (-200b, -200c, -141 and -429), and miR-203 in serum samples from CRC patients with metastasis (Stage IV) and without metastasis (Stage I) by qRT-PCR. The expression of mir-200c and miR-203 were significantly elevated in serum samples from CRC patients with metastasis (Stage IV) compared to patients without metastasis (Stage I).

FIG. 2 is an analysis of the expression of the miR-200 family (-200b, -200c, -141 and -429), and miR-203 in serum samples from CRC patients with metastasis (Stage IV) and without metastasis (Stage I) by qRT-PCR. The expression of mir-200c and miR-203 were significantly elevated in serum samples from CRC patients with metastasis (Stage IV) compared to patients without metastasis (Stage I). These data strongly indicate that our invented miRNAs are useful biomarker for CRC metastasis prediction.

Figure 3:
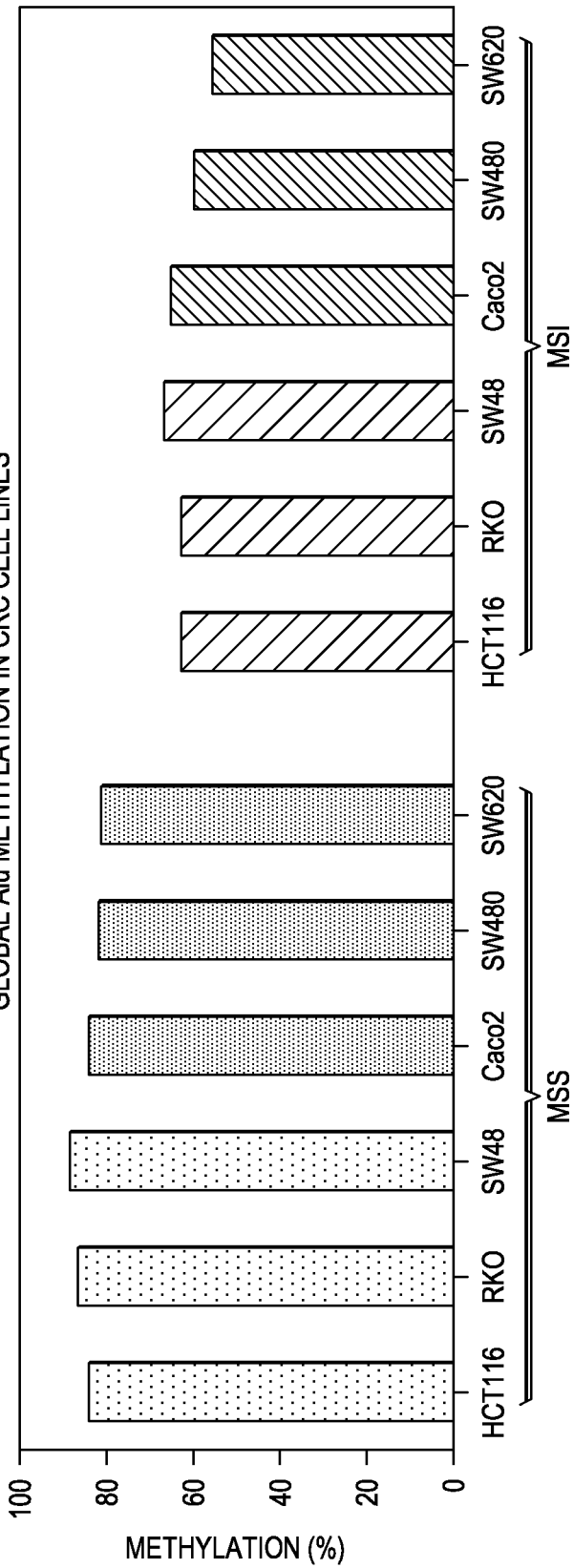
FIG. 3 shows the role of Alu methylation as a surrogate marker for global methylation, CRC cell lines were treated with the demethylating agent (5-azacytidine), which were used to confirm methylation status of global Alu repetitive element by quantitative pyrosequencing for each of the listed CRC cell lines.

FIG. 3 shows the percent methylation the role of Alu methylation as a surrogate marker for global methylation, CRC cell lines were treated with the demethylating agent (5-azacytidine), which were used to confirm methylation status of global Alu repetitive element. Briefly, quantitative pyrosequencing was performed in CRC cell lines. All MSI and MSS CRC cell lines showed hypomethylation of Alu element. The Alu element was markedly demethylated by 5-aza treatment indicating Alu methylation can be used as a global DNA methylation indicator.

Figure 4:
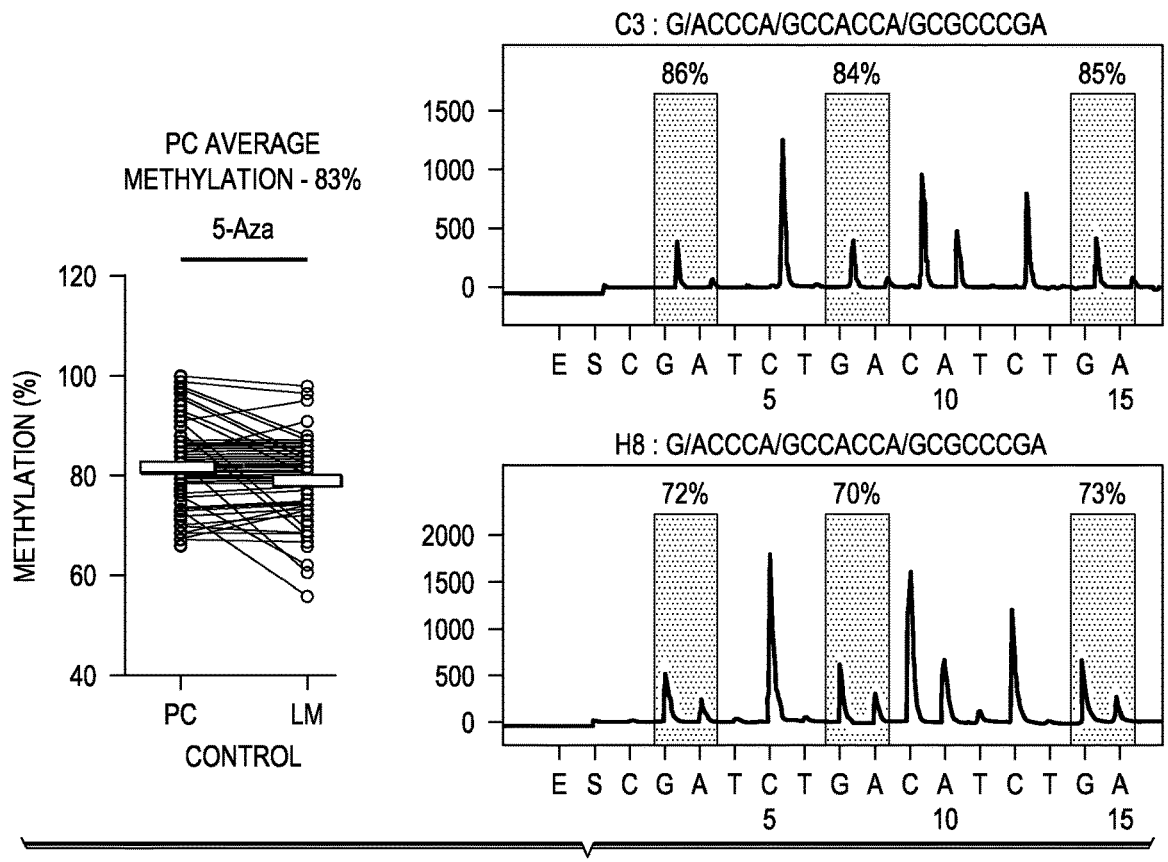
FIG. 4 is an analysis of the global Alu methylation status in matched corresponding primary CRC (PC) and liver metastasized CRC (LM) human tissues by pyrosequencing [SEQ ID NO:1 and SEQ ID NO: 2].

FIG. 4 is an analysis of the global Alu methylation status in matched corresponding primary CRC (PC) and liver metastasized CRC (LM) human tissues by pyrosequencing. LM showed significantly lower Alu methylation compared to PC. This data suggests that Alu hypomethylation is involved in CRC metastasis, which indicates usefulness of Alu methylation as a marker of CRC metastasis. The present inventors analyzed the location of the various miRNAs using the UCSC Genome Browser. Briefly, the miRNA sequences were found in the context of the genome in which they are located and it was found that miR-30b, miR-373, miR-518d, and miR-520c are located downstream of Alu elements (data not shown) (SEQ ID NOs. 1 and 2).

Figure 5A:
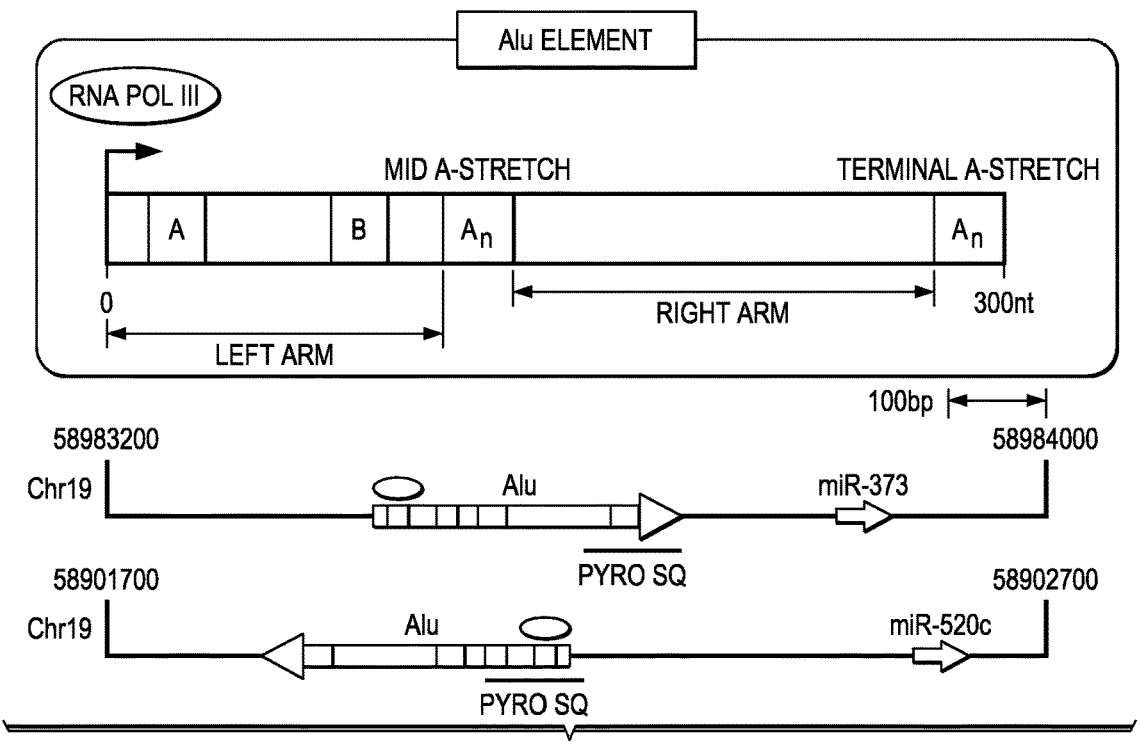
FIG. 5A are maps that show the Alu hypomethylation regulated the expression of down-stream miR-373, but not miR-520c.

FIG. 5A are maps that show the Alu hypomethylation regulated the expression of down-stream miR-373, but not miR-520c.

Figure 5B:
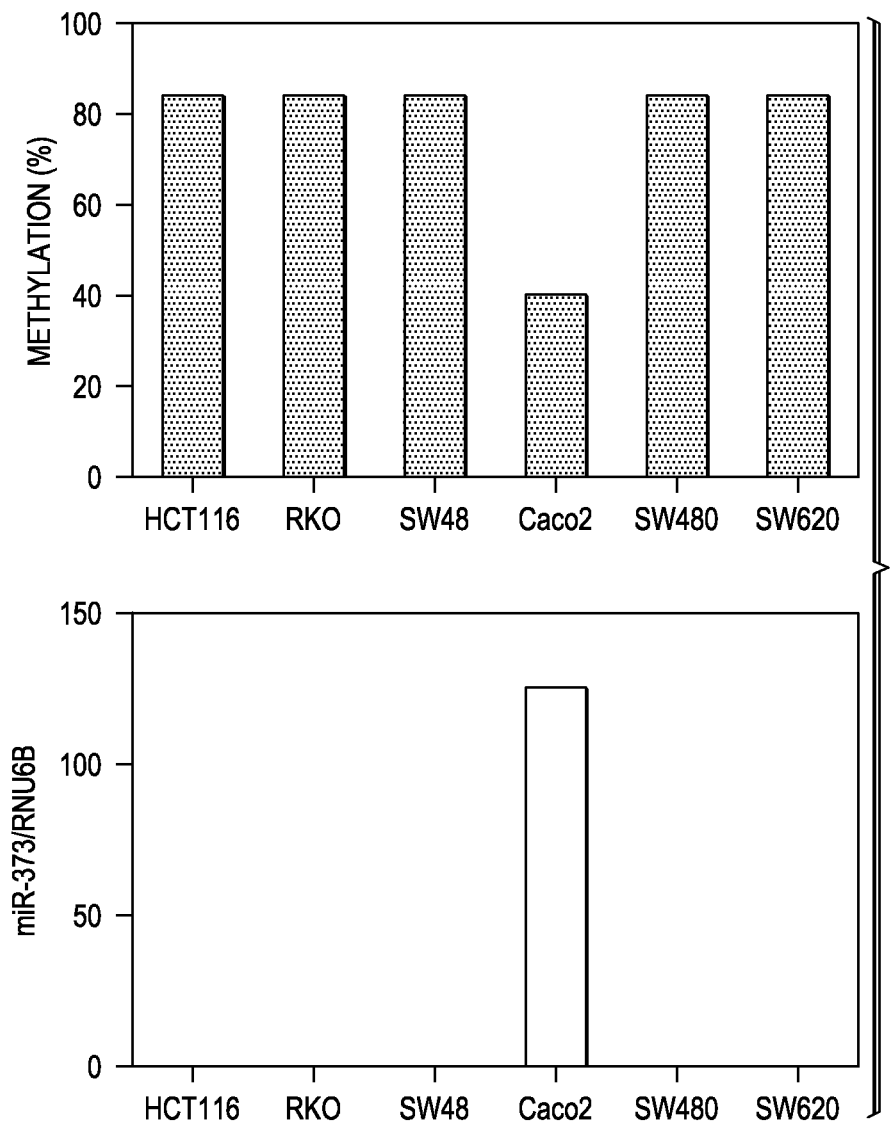
FIG. 5B shows that Alu methylation inversely correlated with miR-373 expression in CRC cell lines.

FIG. 5B shows that Alu methylation inversely correlated with miR-373 expression in CRC cell lines. An analysis of the expression of miR-373 and methylation of Alu (which is located in miR-373 promoter region) in CRC cell lines. It was found that the expression of miR-373 was inversely correlated with Alu methylation. These data demonstrate that miR-373 expression is regulated by promoter region Alu methylation.

Figure 5C:
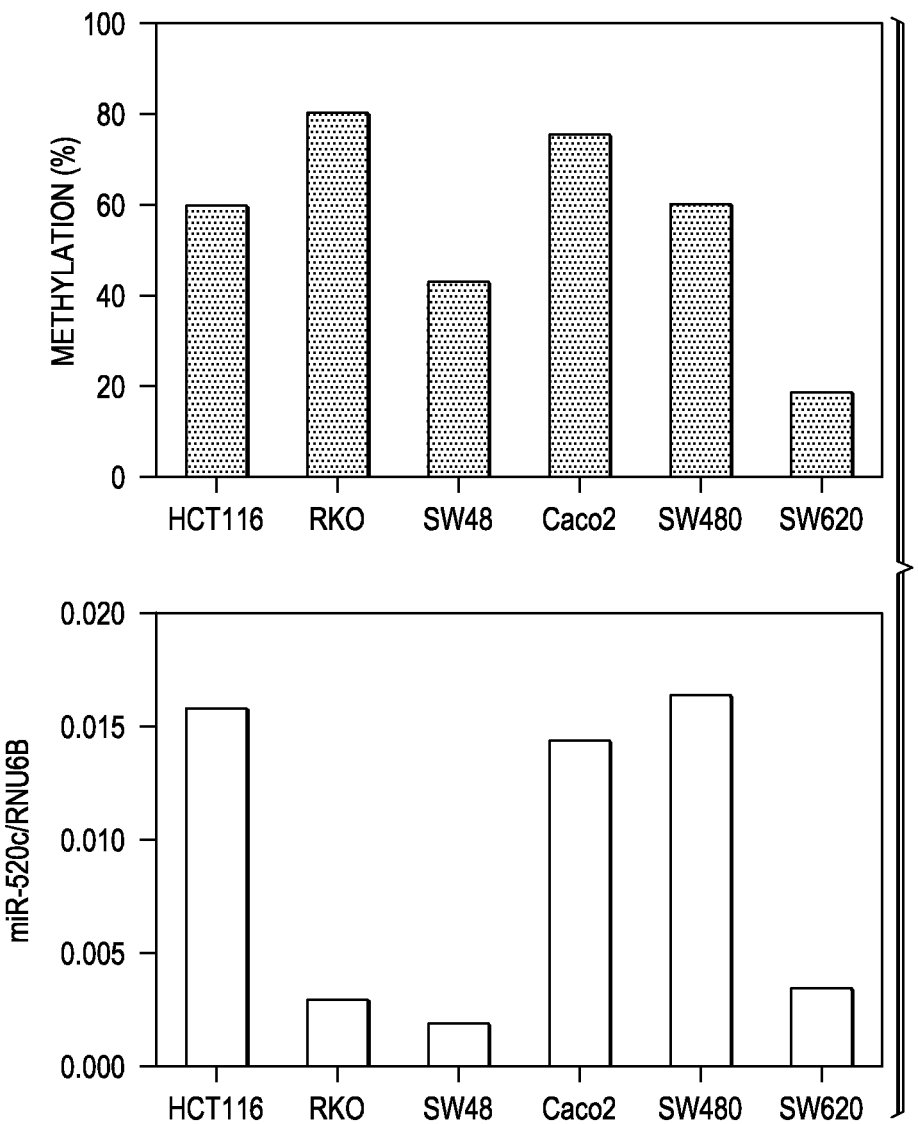
FIG. 5C shows that Alu methylation did not correlate with miR-520c expression in CRC cell lines.

FIG. 5C shows that Alu methylation did not correlate with miR-520c expression in CRC cell lines. The expression of miR-373 was induced by demethylating agent, and Alu element in miR-373 promoter region was demethylated by 5Aza treatment. These data indicate that miR-373 expression is regulated by Alu methylation.

FIG. 6A is an analysis of the expression of miR-520c, which is located in Alu element downstream. All cell lines showed low level of miR-520c expression, except Lovo cell.

FIG. 6B shows that the expression of miR-520c was induced by a demethylating agent. This data indicates that miR-520c expression is regulated by Alu methylation in promoter region.

Figure 7:
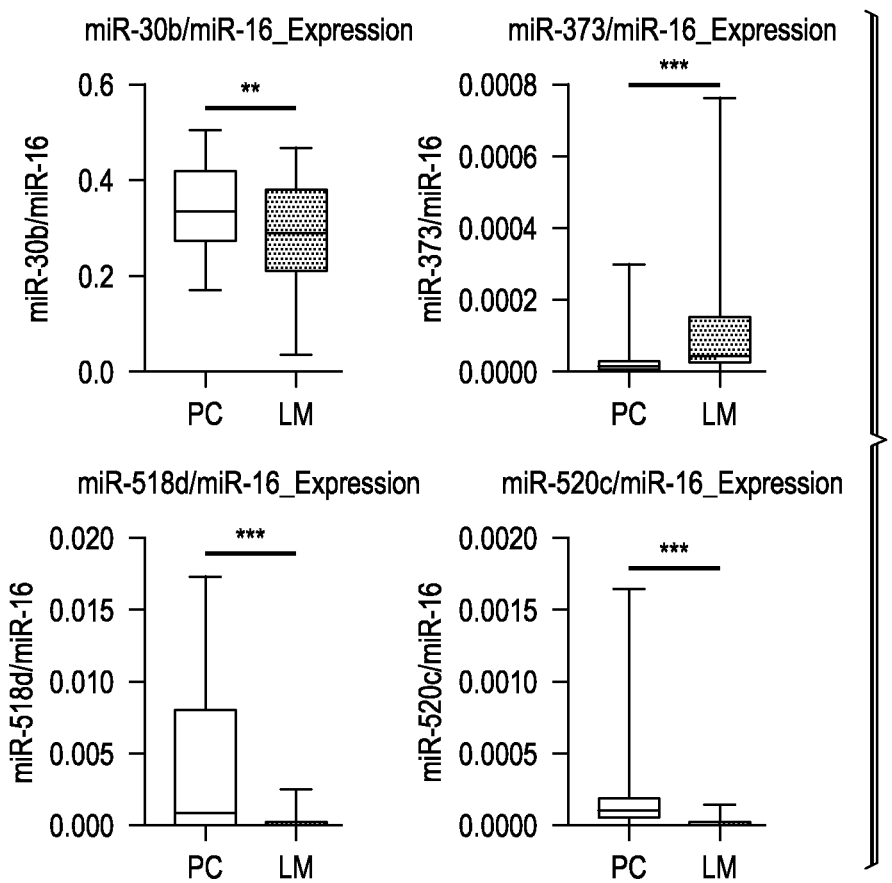
FIG. 7 is an analysis of the expression status all 4 miRNAs that are located downstream of Alu repetitive sequences in matched corresponding primary CRC (PC) and liver metastasized CRC (LM) human tissues by qRT-PCR. LM showed significantly lower expression of miR-30b, miR-518d, and miR-520c compared to PC.

FIG. 7 is an analysis of the expression status all 4 miRNAs that are located downstream of Alu repetitive sequences in matched corresponding primary CRC (PC) and liver metastasized CRC (LM) human tissues by qRT-PCR. LM showed significantly lower expression of miR-30b, miR-518d, and miR-520c compared to PC. On the other hand, miR-373 was significantly up-regulated in LM compared to PC. This data shows that the expression of these four miRNAs distinguished between PC and LM. Moreover, the expression of these four miRNAs expression was regulated by Alu elements methylation, which are located in promoter region.

Figure 8A:
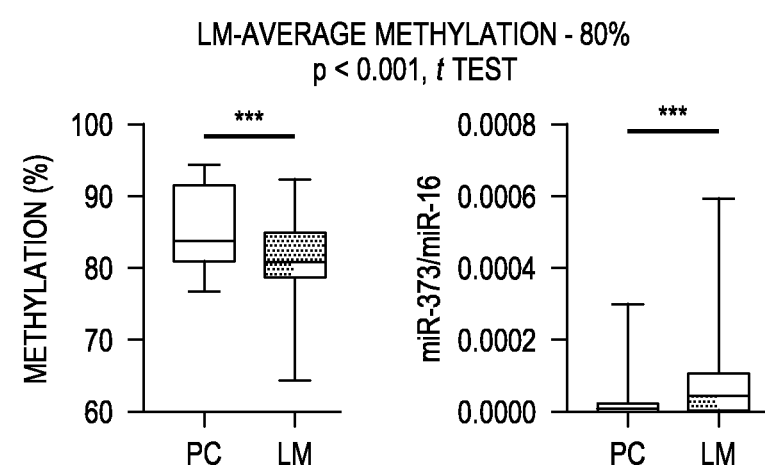
FIG. 8A shows that Alu hypomethylation positively correlated with miR-373 expression in LM.

FIG. 8A shows that Alu hypomethylation positively correlated with miR-373 expression in LM.

FIG. 8B shows that Alu hypomethylation did not correlate with miR-520c expression in LM.

FIG. 9 shows that an RNA pol II inhibitor did not suppress activation of miR-373, but inhibited the expression of miR-520c.

These results show that methylation of Alu repeat elements was not different between MSS and MSI CRC cell lines. Alu methylation in liver metastasized CRC was significantly lower compared to matched primary CRC (80% and 83%, respectively; P<0.001). It was also found that Alu sequences in the promoter region of miR-373 and miR-520c were significantly hypomethylated in liver metastasized CRC compared to matched primary CRC (P<0.05 and P<0.01, respectively). Thus, hypomethylation of Alu elements correlated with the activation and subsequent expression of miR-373, which is transcribed in same direction as Alu elements in liver metastasis tissues compared to matched primary CRC (P<0.01). However, this correlation was not observed for miR-520c that is transcribed in the opposite direction. Finally, treatment of RNA polymerase II inhibitor did not suppress miR-373 transcription, but inhibited the expression of miR-520c.

These figures show that a miRNA signature can be used to distinguish between primary CRC and liver metastasis. It was found that a subset of miRNAs, including: let-7i, miR-10b, miR-30b, miR-200b, miR-320a, and miR-518d were significantly downregulated in liver metastasis tissues compared to primary CRC. In contrast, miRNAs such as miR-141, miR-200c, and miR-203 were significantly overexpressed in liver metastasis tissues. In a further evaluation step using serum samples from CRC patients, it was found that the serum expression levels of miR-200c and miR-203 were upregulated in CRC patients with distant metastasis compared to CRC patients without metastasis.

The methylation status of Alu elements was determined by quantitative bisulfite pyrosequencing, and the expression of miRNAs (miR-30b, miR-373 and miR-520c) was measured by quantitative real-time PCR. Global hypomethylation of Alu sequences was observed by treatment of the DNA demethylating agent, 5-azacytidine, in the CRC cell lines. When the global Alu methylation levels were analyzed in clinical specimens, it was found that the levels of Alu methylation in LM were significantly lower compared to the matched PC (mean methylation value; PC=83% vs. LM=80%; P<0.001). Furthermore, methylation analysis of surrounding normal liver tissues revealed higher levels of Alu methylation (mean methylation value; 85%) when compared to both PC and LM. The expression of miRNAs (miR-30b, miR-373 and miR-520c) located downstream from Alu regions. For example, it was found that miR-373 expression was significantly increased in liver metastasis compared to matching primary CRC clinical samples. In contrast, expression of miR-30b and miR-520c was significantly decreased in liver metastasis when compared to matching primary CRC tissues. These data demonstrate that Alu hypomethylation is involved in CRC distant metastasis, which regulates metastasis-related miRNAs (miR-30b, miR-373 and miR-520c).

Thus, these results show that increased Alu hypomethylation occurs in liver metastasis tissues from patients with CRC. As such, hypomethylation of Alu repeat elements permit activation of metastasis-related miRNAs, which in turn may facilitate a more aggressive malignant phenotype in these advanced stage cancers.

Next, additional studies were conducted to identify the specific subsets of miRNAs that may serve as diagnostic and therapeutic biomarkers for patients with metastatic CRC. A recent and accurate technology to identify novel metastasis related miRNA biomarkers (NANOSTRING®), plus additional studies were conducted to validate screened miRNA biomarkers using two different assay techniques in a large number of CRC tissues.

The screening step included the following materials: 9 pairs of primary CRC (PC) and matched liver metastasis (LM), Frozen tissue, Not-microdissected, method used: NANOSTRING®.

The validation step in matched PCs and LMs included the following materials: 58 pairs of PC and matched LM, formalin-fixed, paraffin-embedded (FFPE) tissue, Microdissected. The method for analysis was TaqMan miRNA assays, miR-16 was used as endogenous control.

A microarray validation step included the following materials: 84 pairs of PC and corresponding normal mucosa (NM), frozen tissue, not-microdissected. The method used was MicroRNA microarray (quadruplicates of 389 human miRNAs) as published in JAMA. 2008 Jan. 30; 299(4):425-36.

A qRT-PCR Validation step included the following materials: 175 PCs, FFPE tissue, microdissected. The method for analysis was TaqMan miRNA assays, with miR-16 used as endogenous control.

Table 1 is a summary of the clinicopathology characteristics of the colorectal cancer patients.

| Characteristics | Clinicopathological characteristics of the colorectal cancer patients | | | |
|---|---|---|---|---|
| | NanoString cohort Patients n = 9 | matched PC and LM validation cohort Patients n = 32 | microarray validation cohort Patients n = 84 | qRT-PCR validation cohort Patients n = 175 |
| Age (Years) | | | | |
| ≤65 | 6 | 34 | 38 | 74 |
| >63 | 3 | 24 | 46 | 101 |
| Sex | | | | |
| Male | 4 | 32 | 66 | 102 |
| Female | 5 | 26 | 18 | 73 |
| Adenocarcinoma histology | | | | |
| Adenocarcinoma* | — | 58 | 75 | 162 |
| Mucinous | — | 0 | 8 | 10 |
| Tumour location | | | | |
| Proximal | — | 12 | 34 | 58 |
| Distal | — | 18 | 48 | 49 |
| Rectum | — | 28 | | 68 |
| TNM stage | | | | |
| I | 0 | 0 | 8 | 38 |
| II | 0 | 7 | 29 | 53 |
| III | 0 | 17 | 36 | 44 |
| IV | 9 | 34 | 10 | 39 |

TABLE 2

Shows the 19 miRNAs differentially expressed in matched PCs and LMs using the NANOSTRING ® screening step.

| Probe from NanoString | Geometric mean | | Fold Change (LM/PC) | FDR (%) | P-value |
|---|---|---|---|---|---|
| | PC (n = 9) | LM (n = 9) | | | |
| hsa-miR-199b-5p | 360.77 | 70.81 | 0.2 | 0.01 | 6.E−05 |
| hsa-let-71 | 2154.94 | 1133.07 | 0.53 | 0.14 | 2.E−03 |
| hsa-miR-484 | 69.79 | 39.14 | 0.56 | 0.14 | 2.E−03 |
| hsa-miR-490-3p | 47.13 | 21.67 | 0.46 | 0.21 | 4.E−03 |
| hsa-miR-122 | 27.01 | 507.91 | 18.8 | 0.26 | 8.E−03 |
| hsa-miR-320a | 33.94 | 22.05 | 0.65 | 0.26 | 8.E−03 |
| hsa-miR-520e | 53.73 | 13.01 | 0.24 | 0.26 | 8.E−03 |
| hsa-miR-10b | 64.28 | 19.67 | 0.31 | 0.27 | 1.E−02 |
| hsa-miR-337-5p | 20.81 | 11.8 | 0.57 | 0.39 | 2.E−02 |
| hsa-miR-485-3p | 89.95 | 50.39 | 0.56 | 0.39 | 2.E−02 |
| hsa-miR-145 | 2915.38 | 1267.64 | 0.43 | 0.39 | 2.E−02 |
| hsa-miR-144 | 294.09 | 116.61 | 0.4 | 0.39 | 2.E−02 |
| hsa-miR-25 | 688.42 | 405.21 | 0.59 | 0.39 | 3.E−02 |
| hsa-miR-221 | 294.27 | 209.8 | 0.71 | 0.39 | 3.E−02 |
| hsa-miR-216a | 59.45 | 34.54 | 0.58 | 0.39 | 3.E−02 |
| hsa-miR-92b | 44.38 | 32.31 | 0.73 | 0.39 | 3.E−02 |
| hsa-miR-365 | 56.55 | 29.25 | 0.52 | 0.39 | 3.E−02 |
| hsa-miR-708 | 269.88 | 155.4 | 0.58 | 0.39 | 3.E−02 |
| hsa-miR-143 | 2652.88 | 1338.82 | 0.5 | 0.39 | 3.E−02 |

Figure 10:
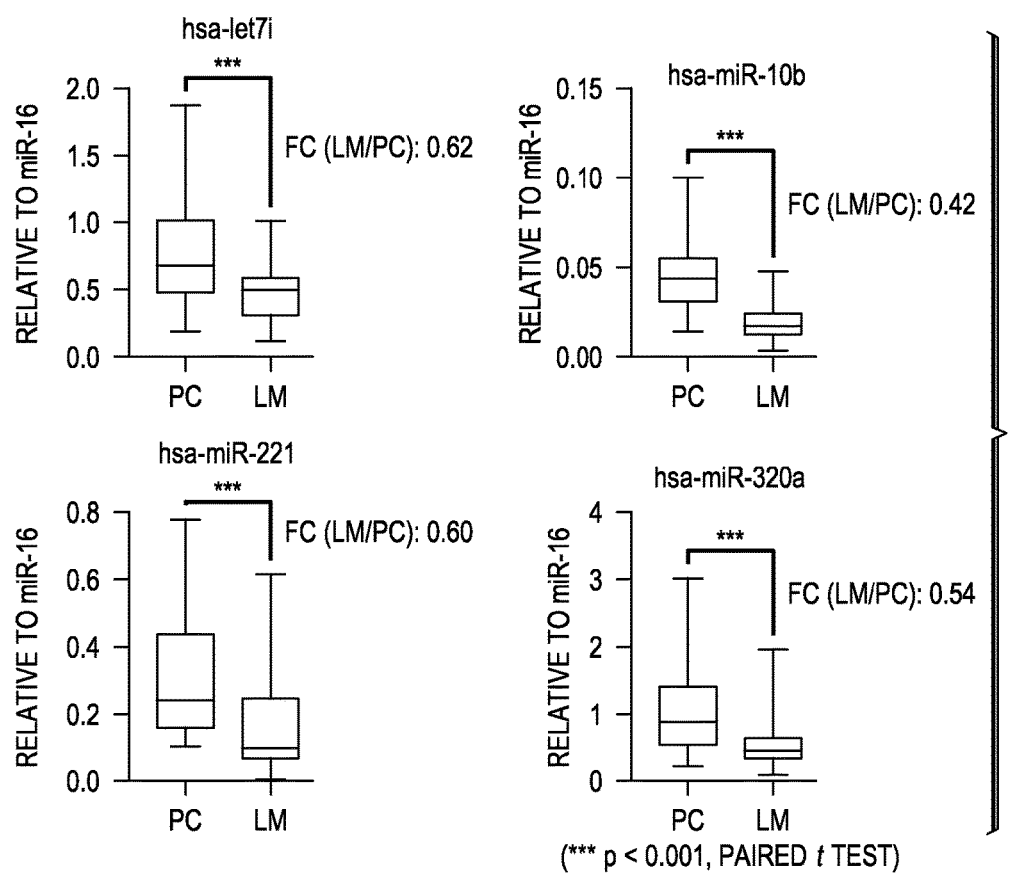
FIG. 10 shows the results of the qRT-PCR validation for selected miRNAs in 58 PCs and LMs.
Figure 11:
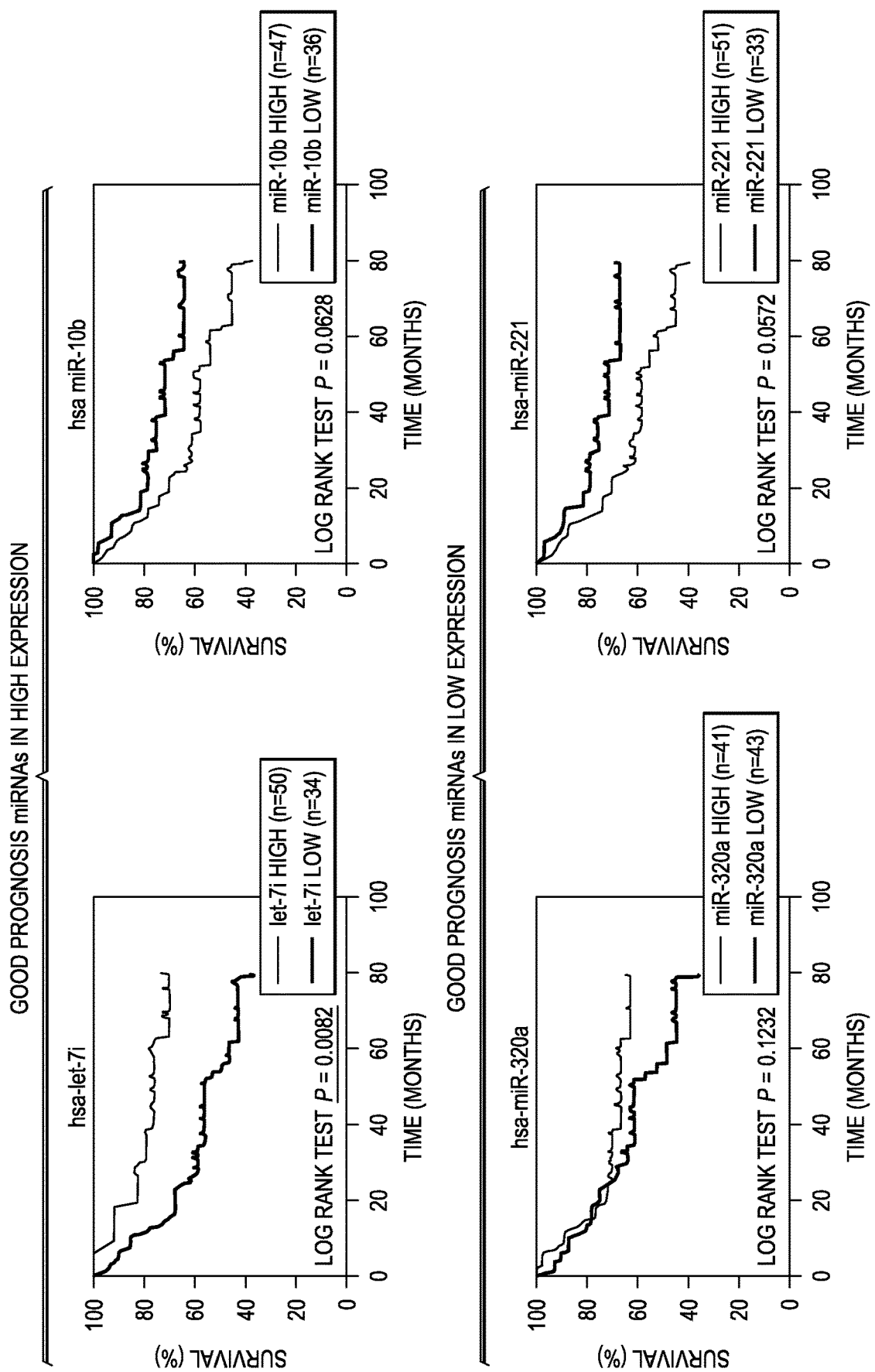
FIG. 11 shows the results from the microarray validation for selected miRNAs in 84 PCs.

FIG. 10 shows the Results—qRT-PCR validation for selected miRNAs in 58 PCs and LMs. FIG. 11 shows the results from the microarray validation for selected miRNAs in 84 PCs (Kaplan-Meier survival curves), in which high expression of has-let-7i and has-miR-320a indicated a good prognosis, which a low expression of has-miR-10b and has-miR-221 indicated a good prognosis.

Table 3 shows the results from the microarray validation for 4 miRNAs in 84 PCs, briefly, it was found that The expression of let-7i, miR-10b and miR-320a in PC was significantly associated with the distant metastasis, while the expression of let-7i and miR-10b was significantly associated with the TNM stage.

Table 4 shows the results of microarray validation for 4 miRNAs in 84 PCs, using a Cox proportional hazards model. It was found that low expression of let-7i was an independent prognostic factor.

| | Good progress miRNAs in high expression | | |
|---|---|---|---|
| | | Univariate | |
| Variables | HR | 95% CI | P |
| Age (>50 vs. ≤50) | 0.7523 | 0.2291 to 2.4704 | 0.6528 |
| Sex (Male vs. Female) | 1.3423 | 0.5605 to 3.2147 | 0.4974 |
| T stage (T3/4 vs. T1/2) | 2.278 | 0.7021 to 7.3914 | 0.1262 |
| N stage (N1/2/3 vs. N0) | 2.9984 | 1.4477 to 6.2100 | 0.0018 |
| M stage (M1 vs. M0) | 3.4586 | 3.6184 to 19.7731 | <0.0001 |
| hsa-let-7i (Low vs. High) | 2.6706 | 1.2577 to 5.6710 | 0.0066 |
| hsa-miR-320s (Low vs. High) | 1.6783 | 0.8655 to 3.2545 | 0.1239 |

| | hsa-let-7i | | | hsa-miR-10b | | |
|---|---|---|---|---|---|---|
| | n | mean ± SD | P value | n | mean ± SD | P value |
| Sex | | | 0.1502 | | | 0.3887 |
| Male | 66 | 0.02407 ± 0.2635 | | 65 | −0.3092 ± 1.1328 | |
| Female | 18 | −0.06910 ± 0.2418 | | 18 | −0.4715 ± 0.9354 | |
| Age (Years) | | | 0.7279 | | | 0.7932 |
| ≤50 | 7 | −0.02879 ± 0.2321 | | 7 | −0.3526 ± 1.0560 | |
| >50 | 77 | 0.007094 ± 0.2641 | | 76 | −0.3436 ± 1.0995 | |
| T stage | | | 0.3125 | | | 0.1248 |
| T1/T2 | 12 | 0.07144 ± 0.2190 | | 12 | −0.8053 ± 1.0168 | |
| T3/T4 | 71 | −0.006089 ± 0.2682 | | 70 | −0.2755 ± 1.0942 | |
| N stage | | | 0.6085 | | | 0.1037 |
| N0 | 38 | 0.03021 ± 0.2648 | | 38 | −0.5572 ± 1.2224 | |
| N1/N2/N3 | 46 | −0.01746 ± 0.2578 | | 45 | −0.1647 ± 0.9403 | |
| M stage | | | 0.0055 | | | 0.0243 |
| M0 | 74 | 0.03081 ± 0.2563 | | 73 | −0.4470 ± 1.0561 | |
| M1 | 10 | −0.1935 ± 0.2090 | | 10 | 0.4043 ± 1.0896 | |
| TNM stage | | | 0.0397 | | | 0.0498 |
| I | 8 | 0.08200 ± 0.2585 | | 8 | −1.0788 ± 1.1221 | |
| II | 29 | 0.02817 ± 0.2658 | | 29 | −0.4334 ± 1.2465 | |
| III | 36 | 0.02464 ± 0.2571 | | 35 | −0.3369 ± 0.8350 | |
| IV | 10 | −0.1935 ± 0.2090 | | 10 | 0.4043 ± 1.0896 | |

| | hsa-miR-221 | | | hsa-miR-320a | | |
|---|---|---|---|---|---|---|
| | n | mean ± SD | P value | n | mean ± SD | P value |
| Sex | | | 0.6947 | | | 0.173 |
| Male | 66 | 0.2713 ± 0.8388 | | 66 | 0.04704 ± 0.3012 | |
| Female | 18 | 0.3753 ± 0.6618 | | 18 | −0.1026 ± 0.3935 | |
| Age (Years) | | | 0.8397 | | | 0.8019 |
| ≤50 | 7 | 0.3691 ± 0.7193 | | 7 | 0.3658 ± 0.1627 | |
| >50 | 77 | 0.2867 ± 0.8126 | | 77 | 0.01302 ± 0.3380 | |
| T stage | | | 0.8359 | | | 0.3187 |
| T1/T2 | 12 | 0.3131 ± 0.7537 | | 12 | 0.09735 ± 0.2206 | |
| T3/T4 | 71 | 0.2900 ± 0.8200 | | 71 | 0.005285 ± 0.3409 | |
| N stage | | | 0.293 | | | 0.1925 |
| N0 | 38 | 0.1865 ± 0.7953 | | 38 | 0.06200 ± 0.2960 | |
| N1/N2/N3 | 46 | 0.3820 ± 0.8046 | | 46 | −0.02386 ± 0.3481 | |
| M stage | | | 0.0868 | | | 0.0498 |
| M0 | 74 | 0.2436 ± 0.7895 | | 74 | 0.03904 ± 0.3240 | |
| M1 | 10 | 0.6632 ± 0.8350 | | 10 | −0.1630 ± 0.3022 | |
| TNM stage | | | 0.3629 | | | 0.1623 |
| I | 8 | 0.1901 ± 0.8263 | | 8 | 0.1268 ± 0.2359 | |
| II | 29 | 0.1778 ± 0.8144 | | 29 | 0.06401 ± 0.2979 | |
| III | 36 | 0.3065 ± 0.7903 | | 36 | 0.008416 ± 0.3614 | |
| IV | 10 | 0.6632 ± 0.8350 | | 10 | −0.1630 ± 0.3022 | |

| | Good progress miRNAs in high expression | | |
|---|---|---|---|
| | Univariate | | |
| Variables | HR | 95% CI | P |
| Age (>50 vs. ≤50) | 0.7523 | 0.2291 to 2.4704 | 0.6528 |
| Sex (Male vs. Female) | 1.3423 | 0.5605 to 3.2147 | 0.4974 |
| T stage (T3/4 vs. T1/2) | 2.278 | 0.7021 to 7.3914 | 0.1262 |
| N stage (N1/2/3 vs. N0) | 2.9984 | 1.4477 to 6.2100 | 0.0018 |
| M stage (M1 vs. M0) | 8.4586 | 3.6184 to 19.7731 | <0.0001 |
| hsa-miR-10b (High vs. Low) | 1.9156 | 0.9681 to 3.8300 | 0.0599 |
| hsa-miR-221 (High vs. Low) | 2.0042 | 0.9687 to 4.1466 | 0.0515 |

Good progress miRNAs in low expression
HR, hazard ratio;
CI, confidence interval Table 5 shows the results of microarray validation for 4 miRNAs in 84 PCs, using a logistic regression model. It was found that all 4 miRNAs (let-7i, miR-320a, miR-10b and miR-221) expression in PCs was significantly associated with the distant metastasis. It was also found that low expression of let-7i and high expression of miR-10b in PCs were an independent metastasis prediction marker, respectively.

| | Univariate | | |
|---|---|---|---|
| Variables | OR | 95% CI | P |
| Good progress miRNAs in high expression | | | |
| Age (>50 vs. ≤50) | 0.7941 | 0.0855 to 7.3728 | 0.8428 |
| Sex (Male vs. Female) | 1.1034 | 0.2129 to 5.7192 | 0.906 |
| T stage (T3/4 vs. T1/2) | 2.05E+07 | 0.0000 to 0.0000 | 0.0673 |
| N stage (N1/2/3 vs. N0) | 9 | 1.0850 to 74.6570 | 0.0102 |
| hsa-let-7i (Low vs. High) | 19.25 | 4.1320 to 89.6808 | 0.0001 |
| hsa-miR-320a (Low vs. High) | 5.5152 | 1.3048 to 23.3120 | 0.0144 |
| Good progress miRNAs in low expression | | | |
| Age (>50 vs. ≤50) | 0.7941 | 0.0855 to 7.3728 | 0.8428 |
| Sex (Male vs. Female) | 1.1034 | 0.2129 to 5.7192 | 0.906 |
| T stage (T3/4 vs. T1/2) | 2.05E+07 | 0.0000 to 0.0000 | 0.0673 |
| N stage (N1/2/3 vs. N0) | 9 | 1.0850 to 74.6570 | 0.0102 |
| hsa-miR-10b (High vs. Low) | 7.625 | 1.8645 to 31.1838 | 0.0044 |
| hsa-miR-221 (High vs. Low) | 9 | 1.0850 to 74.6570 | 0.0102 |

OR, odds ratio;
CI, confidence interval

Figure 12:
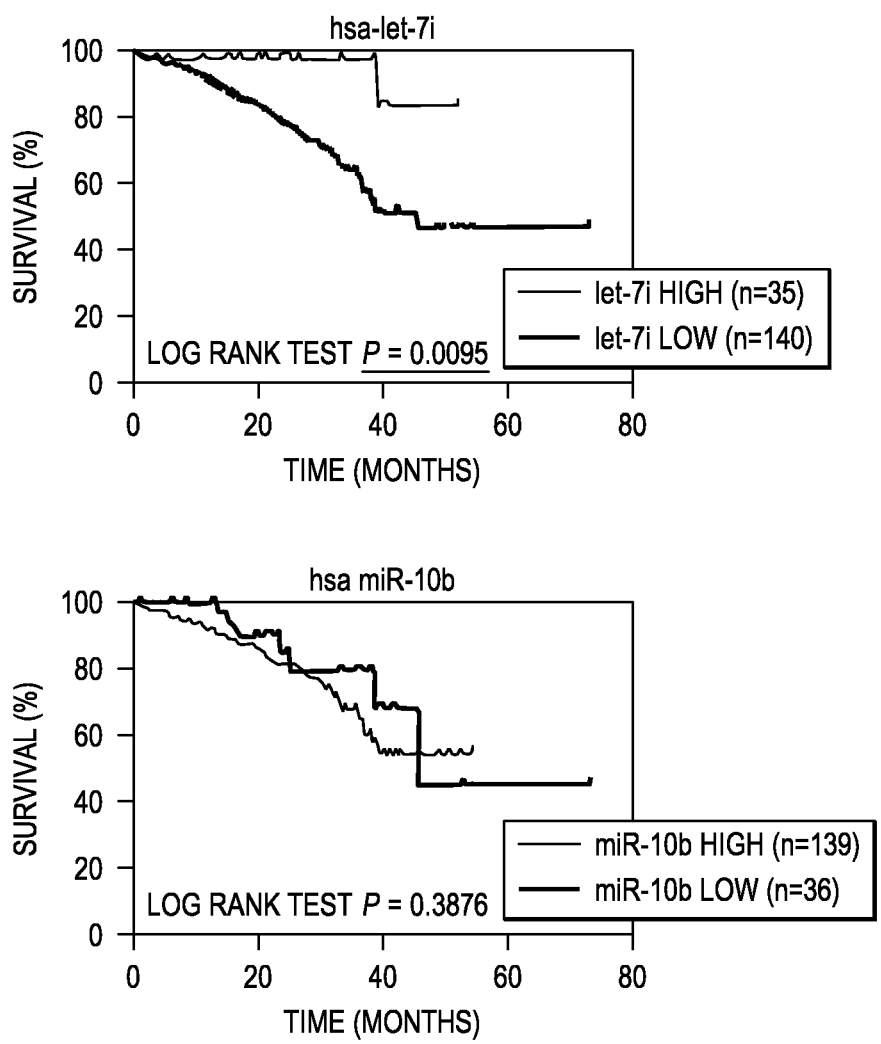
FIG. 12 shows the results of qRT-PCR validation for miR-7i (left graph) and miR-10b (right graph) in 175 PCs.

FIG. 12 shows the results of qRT-PCR validation for miR-7i and miR-10b in 175 PCs. Survival analysis of 2 microarray validated miRNAs is shown.

Table 6 shows the results of qRT-PCR validation for miR-7i and miR-10b in 175 PCs. It was found that the expression of let-7i, miR-10b and miR-320a in PC was significantly associated with the distant metastasis (using the Kreskal-Wallis test). The expression of let-7i and miR-10b was significantly associated with the TNM stage.

| | hsa-let-7i | | | hsa-miR-10b | | |
|---|---|---|---|---|---|---|
| | n | mean ± SD | P value | n | mean ± SD | P value |
| Sex | | | 0.9441 | | | 0.1311 |
| Male | 78 | 0.7862 ± 0.2881 | | 78 | 0.05870 ± 0.02865 | |
| Female | 60 | 0.7956 ± 0.2960 | | 60 | 0.05391 ± 0.03159 | |
| Age (Years) | | | 0.6466 | | | 0.5857 |
| ≤Median | 68 | 0.7938 ± 0.2804 | | 68 | 0.05588 ± 0.03143 | |
| >Median | 70 | 0.7875 ± 0.3012 | | 70 | 0.05734 ± 0.02864 | |
| T stage | | | 0.6927 | | | 0.0183 |
| T1/T2 | 47 | 0.7441 ± 0.1990 | | 47 | 0.04823 ± 0.02788 | |
| T3/T4 | 90 | 0.8081 ± 0.3183 | | 90 | 0.06036 ± 0.02983 | |
| N stage | | | 0.0407 | | | 0.6505 |
| N0 | 85 | 0.8375 ± 0.3025 | | 85 | 0.05571 ± 0.03017 | |
| N1/N2/N3 | 53 | 0.7235 ± 0.2608 | | 53 | 0.05808 ± 0.02981 | |
| M stage | | | <0.0001 | | | 0.0486 |
| M0 | 114 | 0.8517 ± 0.3013 | | 114 | 0.05443 ± 0.02938 | |
| M1 | 24 | 0.6133 ± 0.1562 | | 24 | 0.06701 ± 0.03105 | |
| TNM stage | | | 0.0002 | | | 0.0208 |
| I | 38 | 0.7513 ± 0.2090 | | 38 | 0.04884 ± 0.03021 | |
| II | 43 | 0.8889 ± 0.3261 | | 43 | 0.06255 ± 0.03029 | |
| III | 33 | 0.8896 ± 0.3245 | | 33 | 0.05029 ± 0.02540 | |
| IV | 24 | 0.6133 ± 0.1562 | | 24 | 0.06701 ± 0.03105 | |

Table 7 shows the results from qRT-PCR validation for miR-7i and miR-10b in 175 PCs using the Cox proportional hazards model. It was found that Low expression of let-7i was significantly associated with CRC patient's prognosis, which was an independent prognostic factor.

| | Univariate | | |
|---|---|---|---|
| Variables | OR | 95% CI | P |
| Good progress miRNAs in high expression | | | |
| Age (>Median vs. ≤Median) | 0.5152 | 0.2486 to 1.0677 | 0.0711 |
| Sex (Male vs. Female) | 1.0505 | 0.5094 to 2.1662 | 0.8938 |
| T stage (T3/4 vs. T1/2) | 6.07E+00 | 1.7714 to 20.7823 | 0.0005 |
| N stage (N1/2/3 vs. N0) | 25.6744 | 7.4879 to 88.0324 | <0.0001 |
| hsa-let-7i (Low vs. High) | 5.9853 | 1.3679 to 26.1892 | 0.0031 |
| Good progress miRNAs in low expression | | | |
| Age (>Median vs. ≤Median) | 0.5152 | 0.2486 to 1.0677 | 0.0711 |
| Sex (Male vs. Female) | 1.0505 | 0.5094 to 2.1662 | 0.8938 |
| T stage (T3/4 vs. T1/2) | 6.07E+00 | 1.7714 to 20.7823 | 0.0005 |

-continued

|  | Univariate | | |
| --- | --- | --- | --- |
| Variables | OR | 95% CI | P |
| N stage (N1/2/3 vs. N0) | 25.6744 | 7.4879 to 88.0324 | <0.0001 |
| hsa-miR-10b (High vs. Low) | 2.8624 | 0.8176 to 10.0217 | 0.05 |

OR, odds ratio;
CI, confidence interval

Table 8 shows the results from qRT-PCR validation for miR-7i and miR-10b in 175 PCs using a logistic regression model. It was found that expression of let-7i and miR-10b in PCs was significantly associated with the distant metastasis. Low expression of let-7i and high expression of miR-10b in PCs were an independent metastasis prediction marker, respectively.

|  | Univariate | | |
| --- | --- | --- | --- |
| Variables | HR | 95% CI | P |
| Good prognosis mRNAs in high expression | | | |
| Age (>Median vs. ≤Median) | 0.8034 | 0.4370 to 1.4772 | 0.4816 |
| Sex (Males vs. Female) | 1.1504 | 0.6133 to 2.1576 | 0.662 |
| T stage (T3/4 vs. T1/2) | 7.9376 | 1.9318 to 32.6160 | 0.0001 |
| Lymph node metastasis (Yes vs. No) | 15.179 | 5.4217 to 42.4966 | <0.0001 |
| Liver metastasis (Yes vs. No) | 12.0601 | 6.0761 to 23.9370 | <0.0001 |
| Pathology (Poor diff. vs. Well/Mod diff.) | 1.8409 | 0.7747 to 4.3745 | 0.2005 |
| CEA (>Median vs. ≤Median) | 5.4597 | 2.2795 to 13.0769 | <0.0001 |
| hsa-let-7i (Low vs. High) | 5.3525 | 1.3009 to 22.0225 | 0.0026 |
| Good prognosis mRNAs in low expression | | | |
| Age (>Median vs. ≤Median) | 0.8034 | 0.4370 to 1.4772 | 0.4816 |
| Sex (Males vs. Female) | 1.1504 | 0.6133 to 2.1576 | 0.662 |
| T stage (T3/4 vs. T1/2) | 7.9376 | 1.9318 to 32.6160 | 0.0001 |
| Lymph node metastasis (Yes vs. No) | 15.179 | 5.4217 to 42.4966 | <0.0001 |
| Liver metastasis (Yes vs. No) | 12.0601 | 6.0761 to 23.9370 | <0.0001 |
| Pathology (Poor diff. vs. Well/Mod diff.) | 1.8409 | 0.7747 to 4.3745 | 0.2005 |
| CEA (>Median vs. ≤Median) | 5.4597 | 2.2795 to 13.0769 | <0.0001 |
| hsa-miR-10b (High vs. Low) | 1.7849 | 0.7283 to 4.3747 | 0.1946 |

HR, hazard ratio;
CI, confidence interval

Figure 13:
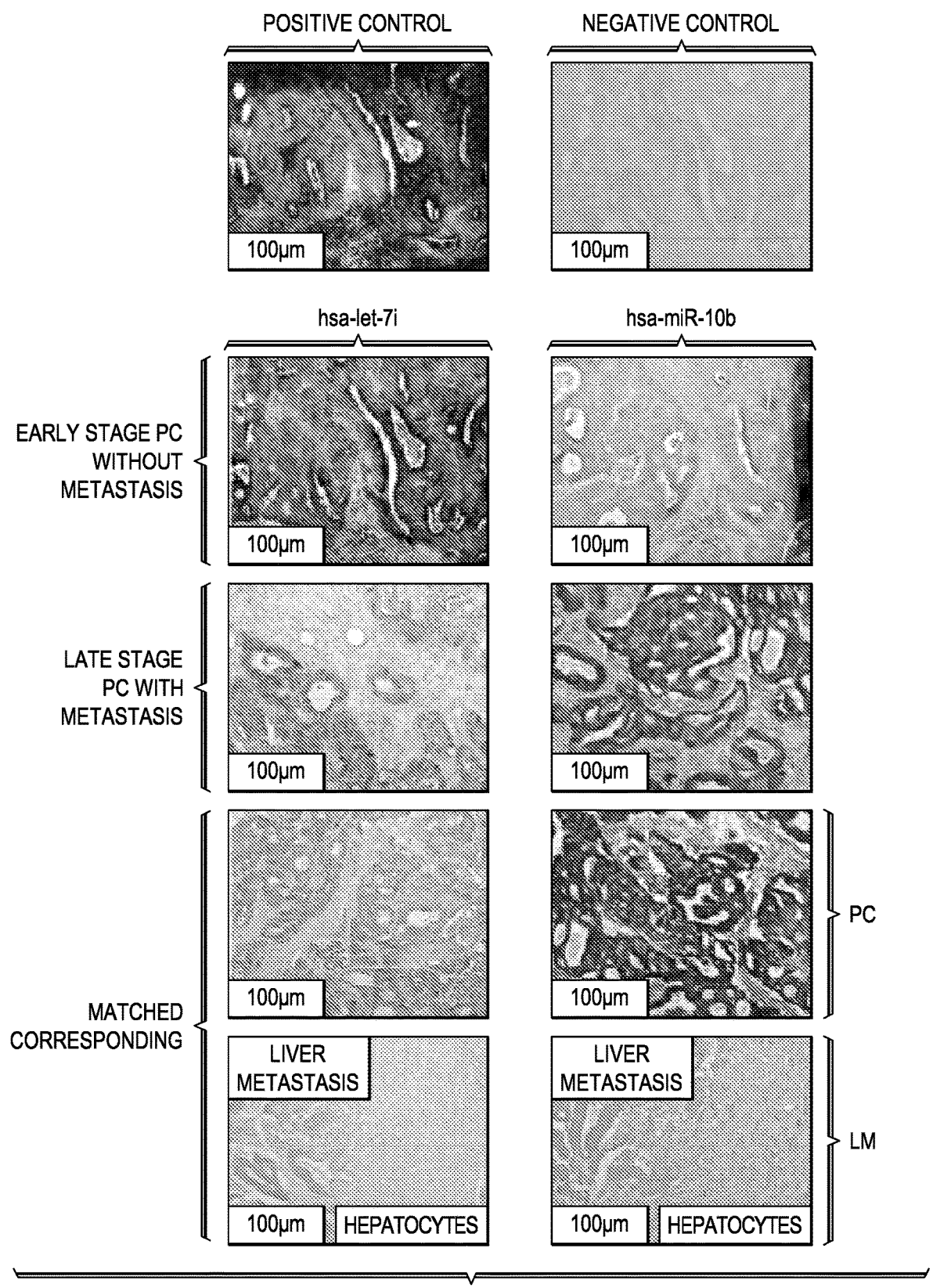
FIG. 13 shows the ISH validation for the expression of miR-7i and miR-10b in CRC tissues and liver metastasis.

FIG. 13 shows the ISH validation for the expression of miR-7i and miR-10b in CRC tissues and liver metastasis.

As such, it was found that 19 metastasis specific miRNAs were identified through screening step using NANOS-TRING® analysis. Among 19 screened miRNAs, 4 miRNAs were validated in a large number of matched PC and LM tissues (58 pairs). High expression of let-7i was significantly associated with better survival, which was an independent prognostic marker in CRC patients. Low expression of let-7i and high expression of miR-10b were independent metastasis prediction markers in PCs, respectively. Finally, it was found that let-7i and miR-10b expression was successfully validated through ISH analysis in CRC tissues.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for treating a patient with Stage IV colorectal cancer, the method comprising:
    treating the patient with adjunctive therapy;
    wherein the patient comprises one that has been determined to have a statistically significantly lower expression level of let-7i and/or miR-320a in a biological sample from the patient, as compared to a control sample, and/or when the patient was determined to have a statistically significantly higher expression level of miR-10b, miR-221, miR-200c, and/or miR-203 in a biological sample from the patient, as compared to a control; wherein the expression level in the biological sample was determined by performing digital color-coded barcode technology analysis, microarray expression profiling, PCR, reverse transcriptase PCR, reverse transcriptase real-time PCR, quantitative real-time PCR, end-point PCR, multiplex end-point PCR, cold PCR, ice-cold PCR, mass spectrometry, or nucleic acid sequencing on nucleic acids from the biological sample from the patient; wherein the control sample is a reference level of expression from a biological sample of a patient with Stage I colorectal cancer.

2. The method of claim 1, wherein the biological sample from the patient comprises a tissue sample from a colorectal cancer primary tumor from the patient or a serum sample the patient.

3. The method of claim 1, wherein the patient was determined to have at least 50% lower expression level of let-7i or miR-320a as compared to the control or was determined to have at least 50% higher expression level of miR-10b, miR-221, miR-200c, or miR-203 as compared to the control.

4. The method of claim 1 wherein the patient was determined to have a statistically significantly lower expression level of let-7i sample as compared to the control.

5. The method of claim 1 wherein the patient was determined to have statistically significantly higher expression level of miR-10b as compared to the control.

6. The method of claim 1, wherein the patient was determined to have statistically significantly lower expression level of let-7i as compared to a control and was determined to have statistically significantly higher expression level of miR-10b as compared to a control.

7. The method of claim 1 wherein the patient was determined to have statistically significantly lower expression level of one or more of miR-320a and miR-221 as compared to the control.

8. The method of claim 1, wherein the patient was determined to have statistically significantly lower expression levels of let-7i and miR320a as compared to the control and was determined to have statistically significantly higher expression levels of miR-10b and miR-221 as compared to the control and wherein the expression level was determined in a tissue sample from a colorectal cancer primary tumor from the patient.

9. The method of claim 1, wherein the adjunctive therapy comprises 5-fluorouracil and/or leucovorin.

10. A method for treating a patient with colorectal cancer, the method comprising:
    treating the patient with adjunctive therapy;
    wherein the patient was determined to have statistically significantly higher expression level of miR-200c and/or miR-203 in a serum sample from the patient as compared to the level of expression of miR-200c and miR-203 in serum from Stage I colorectal cancer patients; wherein the expression level in the biological sample was determined by performing digital color-coded barcode technology analysis, microarray expression profiling, PCR, reverse transcriptase PCR, reverse transcriptase real-time PCR, quantitative real-time PCR, end-point PCR, multiplex end-point PCR, cold PCR, ice-cold PCR, mass spectrometry, or nucleic acid sequencing on nucleic acids from the biological sample from the patient.

11. The method of claim 10, wherein both miR-200c and miR-203 are detected, and wherein the patient was determined to have statistically significantly higher expression level of both of miR-200c and miR-203.

12. The method of claim 10, wherein the adjunctive therapy comprises 5-fluorouracil and/or leucovorin.

13. The method of claim 10, wherein the method is for treating metastatic colorectal cancer.

14. The method of claim 13, wherein the metastatic colorectal cancer comprises liver metastasis.

15. The method of claim 10, wherein the patient has been diagnosed with colorectal cancer.

16. The method of claim 10, wherein the patient has not been diagnosed as having metastatic colorectal cancer.

17. A method for detecting the expression level of one or more RNAs selected from let-7i, miR-10b, miR-320a, and miR-221, miR-200c, and miR-203 in a sample from a patient having or suspected of having colorectal cancer, the method comprising:
 a. detecting the expression level of the one or more RNAs in a biological sample from the patient by contacting the sample with a probe that specifically binds to the one or more RNAs and detecting binding between the probe and the RNA in the sample; and
 b. comparing the level of expression of the one or more detected RNAs in the biological sample from the human patient having colorectal cancer to a control; wherein the control is the expression level of the one or more detected RNAs in a biological sample from patients with Stage I colorectal cancer.

18. The method of claim 17, wherein the biological sample from the human patient having colorectal cancer and the biological sample of the control is a serum sample and wherein the one or more RNAs comprise miR-200c and miR-203.

19. The method of claim 17, wherein the level of expression of miR-200c and miR-203 in the serum sample from the human patient having colorectal cancer is detected by digital color-coded barcode technology analysis, microarray expression profiling, PCR, reverse transcriptase PCR, reverse transcriptase real-time PCR, quantitative real-time PCR, end-point PCR, multiplex end-point PCR, cold PCR, ice-cold PCR, mass spectrometry, or nucleic acid sequencing.

20. The method of claim 17, wherein the patient has been diagnosed with colorectal cancer.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
gacccagcca ccagcgcccg a                                          21

<210> SEQ ID NO 2
<211> LENGTH: 15
<212> TYPE: DNA
<213> ORGANISM: Artificial Sequence
<220> FEATURE:
<223> OTHER INFORMATION: Synthetic Primer

<400> SEQUENCE: 2
cgatctgaca tctga                                                 15
```